US008329402B2

(12) United States Patent
Chaillou et al.

(10) Patent No.: US 8,329,402 B2
(45) Date of Patent: Dec. 11, 2012

(54) **COMBINATION OF MARKER GENES FOR CHARACTERIZING A *LACTOBACILLUS SAKEI* STRAIN**

(75) Inventors: Stéphane Chaillou, Orgerus (FR); Monique Zagorec, Orsay (FR); Marie-Christine Champomier-Verges, Sceaux (FR)

(73) Assignee: Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 12/920,057

(22) PCT Filed: Feb. 20, 2009

(86) PCT No.: PCT/EP2009/052075
§ 371 (c)(1),
(2), (4) Date: Aug. 27, 2010

(87) PCT Pub. No.: WO2009/106491
PCT Pub. Date: Sep. 3, 2009

(65) Prior Publication Data
US 2011/0172112 A1    Jul. 14, 2011

Related U.S. Application Data

(60) Provisional application No. 61/031,763, filed on Feb. 27, 2008.

(30) Foreign Application Priority Data

Feb. 27, 2008  (EP) .................................... 08300118

(51) Int. Cl.
*C12Q 1/00* (2006.01)
*C12Q 1/68* (2006.01)
(52) U.S. Cl. ............ 435/6.1; 435/4; 435/6.12; 435/6.15
(58) Field of Classification Search .................. None
See application file for complete search history.

(56) References Cited

FOREIGN PATENT DOCUMENTS

| EP | 2 096 180 | 9/2009 |
|---|---|---|
| WO | WO 2005/103294 | 11/2005 |
| WO | WO 2009/106491 | 9/2009 |

OTHER PUBLICATIONS

Alpert et al. (Sep. 2003) "Characterization of a Theta-Type Plasmid from *Lactobacillus sakei*: A Potential Basis for Low-Copy-Number Vectors in Lactobacilli," *Appl. Environ. Microbiol.* 69(9):5574-5584.
Ammor S. et al. (Dec. 2005) "Characterization and selection of *Lactobacillus sakei* strains isolated from traditional dry sausage for their potential use as starter cultures," *Food Microbiology* 22(6):529-538.
Anonymous, material downloaded Feb. 21, 2011 from url: http://omad.operon.com/download/index.php cited in International Search Report for PCT/EP2009/052075.
Anonymous, materials downloaded Feb. 21, 2011 from url: http://omad.operon.com/download/storage/lactobacillus_sakei_V1.0.2_dataheet.pdf cited in International Search Report for PCT/EP2009/052075.
Berthier et al. (Aug. 1996) "Polymorphic Restriction Patterns of Ribosomal Internal Transcribed Spacers in the Biocontrol Fungus *Puccinia carduorun* Correlate with Weed Host Origin," *Appl. Environ. Microbiol.* 62(8):3037-3041.
Berthier et al. (1999) "Genetic Diversity within *Lactobacillus sakei* and *Lactobacillus curvatus* and Design of PCR Primers for its Detection Using Randomly Amplified Polymorphic DNA," *Int. J. Syst. Bacteriol.* 49:997-1007.
Chaillou S. et al. (Dec. 2005) "The complete genome sequence of the meat-bourne lactic acid bacterium *Lactobacillus sakei* 23K" *Nature Biotechnology* vol. 23(12) 1527-1533.
Chaillou S. et al. (Dec. 2008) "Intraspecies Genomic Diversity and Natural Population Structure of the Meat-Bourne Lactic Acid Bacterium *Lactobacillus sakei*," *Applied Environmental Microbiology* 75(4): 970-980.
Dudez et al. (Feb. 2002) "Physical and Genetic Map of the *Lactobacillus sakai* 23K Chromomsome," *Microbiology* 148:421-431.
EP search report for EP application 08300118.0 dated Apr. 16, 2010, published as EP2096180.
International Search report PCT/EP2009/052075, published Sep. 3, 2009.
International Preliminary Report on Patentability (IPRP) for PCT/EP2009/052075, issued Aug. 31, 2010.
Joffraud et al. (Oct. 15, 2006) "Effect of Bacterial Interactions on the Spoilage of Cold-Smoked Salmon," *Int. J. Food Microbiol.* 112(1):51-61.
Klein et al. (Apr. 1996) "Emended Descriptions of *Lactobacillus sake* (Katagigi, Kitahara, and Fukami) and *Lactobacillus curvatus* (Abo-Elnaga and Kandler): Numerical Classification Revealed by Protein Fingerprinting and Identification Based on Biochemical Patterns and DNA-DNA Hybridizations," *Int. J. Syst. Bacteriol.* 46:367-376.
Lauret et al. (Jun. 1996) "Carbohydrate Utilization in *Lactobacillus sake*," *Appl. Environ. Microbiol.* 62(6):1922-1927.
Marceau et al. (Dec. 2004) "Evidence for Involvement of at Least Six Proteins in Adaptation of *Lactobacillus sakei* to Cold Temperatures and Addition of NaCl," *Appl. Environ. Microbiol.* 70(12):7260-7268.
Sharp et al. (1987) "The Codon Adaptation Index—A Measure of Directional Synonymous Codon Usage Bias, and Its Potential Applications," *Nuc. Acids Res.* 15(3):1281-1295.
Vermeiren et al. (Nov. 2004) "Evaluation of meat borne lactic acid bacteria as protective cultures for the biopreservation of cooked meat products," *Int'l J. Food Microbiol.* 96:149-164.
Walter et al. (Jun. 2001) "Detection of *Lactobacillus, Pediococcus, Leuconostoc,* and *Weissella* Species in Human Feces by Using Group-Specific PCR Primers and Denaturing Gradient Gel Electrophoresis," *Appl. Environ. Microbiol.* 67(6):2578-2585.

*Primary Examiner* — Ardin Marschel
*Assistant Examiner* — Addison D Ault
(74) *Attorney, Agent, or Firm* — Greenlee Sullivan P.C.

(57) ABSTRACT

The present invention relates to a new combination of marker genes for characterizing a *Lactobacillus sakei* strain. In particular, the present invention concerns the use of a pattern of presence or absence of marker genes in the genome of the strain to be characterized for classifying and identifying said strain.

16 Claims, 4 Drawing Sheets

COMBINATION OF MARKER GENES FOR CHARACTERIZING A *LACTOBACILLUS SAKEI* STRAIN

CROSS-REFERENCE TO RELATED APPLICATIONS

This application is a U.S. National Stage application of international application PCT/EP2009/052075, filed in English on Feb. 20, 2009, which designated the United States, and which claims the benefit of European patent application 08300118.0, filed Feb. 27, 2008 and U.S. provisional application 61/031,763, filed Feb. 27, 2008. Each of these applications is incorporated by reference herein in its entirety.

FIELD OF THE INVENTION

The present invention relates to a combination of marker genes for characterizing a *Lactobacillus sakei* strain. In particular, the present invention concerns the use of a pattern of presence or absence of marker genes in the genome of the strain to be characterized for classifying and identifying said strain.

BACKGROUND OF THE INVENTION

Fresh meat and fish are nutritious but highly perishable foods. During production and storage they are exposed to unavoidable microbial contamination from the processing environment. Such contamination may include spoilage organisms and pathogens. It is therefore a priority for food processors to restrict the growth of contaminants so that they do not develop to potentially dangerous levels. One of the methods employed is the use of safe bacteria to curb growth of spoilage and disease-causing micro-organisms. The meat-borne lactic acid bacterium *Lactobacillus sakei* shows in this view excellent properties.

*L. sakei* has the ability to survive and grow on fresh meat, forming the dominant population when selective techniques are applied. Some strains are widely used in Europe for artisanal and larger scale manufacture of fermented sausages because of their useful preservative properties. But they could also be used as meat biopreservative by preventing the growth of unwanted bacteria (Vermeiren et al. 2004 *Int. J. Food Microbiol.* 96:149-164).

Strains of *L. sakei* can display an important variability in phenotypic traits and have for long been considered difficult to classify. Previous studies have disclosed approaches for *L. sakei* strains classification. Studies using numerical analysis of RAPD patterns (Berthier and Ehrlich 1999 *Int. J. Syst. Bacteriol.* 49:997-1007) or SDS-PAGE soluble protein content patterns have suggested the division of the strains into two subgroups, although weakly defined and not comparable according to the studies.

Thus, *L. sakei* strains classification obtained through these approaches remains unsatisfactory. An aim of the present invention is to provide better methods of classification, characterization and identification of *L. sakei* strains, which could in particular be used to identify *L. sakei* strains present on food or in a cocktail of bacteria used as biopreservative.

The inventors of the present invention have herein identified, based on an in silico study of the *L. sakei* genome and on experimental validation on a large collection of *L. sakei* strains, a combination of markers for characterizing and detecting these strains. In particular, 29 marker genes have been isolated, whose combination provides an optimal way of characterizing *L. sakei* strains.

SUMMARY OF THE INVENTION

The present invention thus relates to a combination of markers enabling for characterizing a *L. sakei* strain which comprises at least two marker genes selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29).

In a preferred embodiment, said combination comprises all of the marker genes SEQ ID NO:1 to SEQ ID NO:29.

The present invention also relates to a method for characterizing a *L. sakei* strain which comprises the step consisting of determining the presence or absence of at least one marker gene selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29) in said *L. sakei* strain.

In a preferred embodiment, the presence or absence of all of said marker genes SEQ ID NO: 1 to SEQ ID NO: 29 is determined.

Preferably, the presence or absence of said marker gene(s) is determined by amplification, or by hybridization with probes specific of said marker gene(s).

In a preferred embodiment, a classification of said *L. sakei* strain is performed by analyzing the pattern of presence or absence of the above marker gene(s) and calculating a Jaccard index or Dice Coefficient or any binary distance matrix with regard to a set of reference *L. sakei* strains.

The present invention also concerns a DNA array which comprises a combination of markers as defined above.

Another aspect of the present invention concerns a method of comparing at least two *L. sakei* strains comprising the steps consisting of a) determining the presence or absence of at least one marker gene selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29), in a first *L. sakei* strain, and b) determining the presence or absence of said at least one marker gene in a second *L. sakei* strain, wherein, if the pattern of presence or absence of said at least one marker gene is different between said first and said second *L. sakei* strains, then the *L. sakei* strains are different.

In a preferred embodiment, the presence or absence of all of said marker genes SEQ ID NO: 1 to SEQ ID NO: 29 is determined.

In a particular embodiment, the above method of comparing at least two *L. sakei* strains further comprises the step of analysing the pattern of presence or absence of said marker genes by calculating a Jaccard index, or a Dice coefficient or any binary distance matrix.

Another aspect of the present invention relates to a method of quantifying a specific *L. sakei* strain in a sample comprising the steps consisting of:

a) identifying and/or characterizing the *L. sakei* strains present in said sample by a method as defined above, b) determining the marker gene(s) which is(are) differently present in said specific L. strain with respect to other strains present in said sample, and c) amplifying said gene(s) by quantitative PCR.

DETAILED DESCRIPTION OF THE INVENTION

In order to identify marker genes that could be used to characterize specifically a *L. sakei* strain compared with other *L. sakei* strains, the inventors first identified variable genomic islands in the genome of *L. sakei* 23K that were likely to contain variable genes displaying a high diversity according to the species (step described in Example 1). Then, they performed a classification of *L. sakei* strains according to the presence or absence of genes from genomic islands previously identified and compared the so obtained classification with the one obtained using several other typing techniques (step described in Example 2). Finally, they identified an optimal combination of a minimum number of genes from the genomic islands that could be used to obtain a reliable classification of *L. sakei* strains compared to the one obtained with a high number of variable genes (step described in Example 3).

Accordingly, according to the invention, a combination of markers enabling for characterizing a *L. sakei* strain comprises at least two marker genes selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29).

As used herein, the term—marker—refers to any biological, chemical or physical mean allowing identifying the presence, and possibly quantifying the expression of a target gene in a bacterial strain. Such markers are well known from one skilled in the art. Advantageously, the markers according to the invention are gene markers.

Table 1 gives the correspondence between the above referenced locus tag and sequence of marker genes and the name of the genes.

The presence or absence of one or a combination of some of these genes can be used to discriminate a particular *L. sakei* strain from another closely related strain.

As described in Example 3, the inventors have demonstrated that these 29 marker genes were optimal to characterize a *L. sakei* strain among other *L. sakei* strains. Therefore, in a preferred embodiment, said combination consists of the marker genes SEQ ID NO: 1 to SEQ ID NO: 29.

Figure 3:
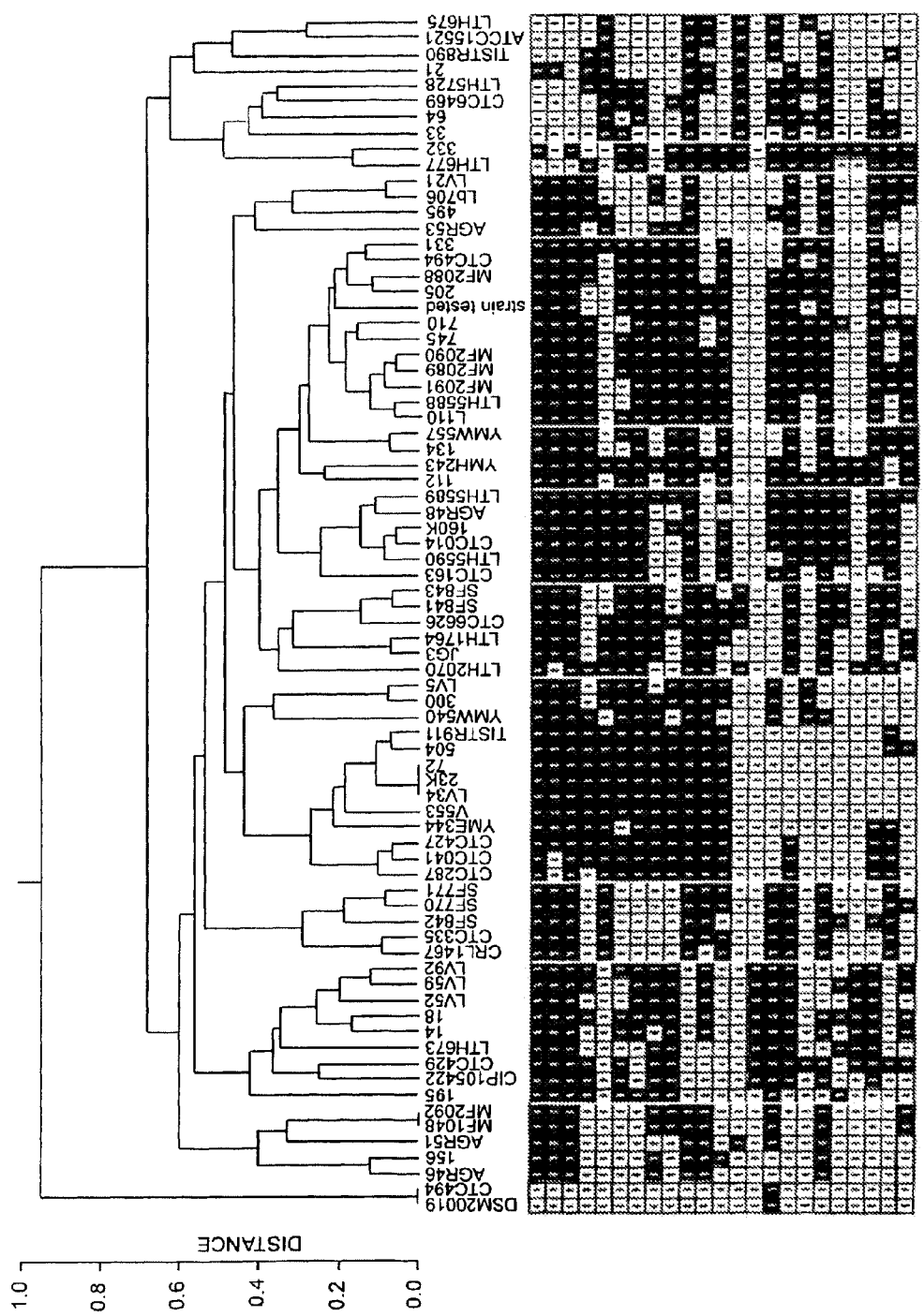
FIG. 3: Dendrogram showing estimates of genomic relationships of the strains was constructed by complete linkage hierarchical analysis. The scale represents the distance at each node. Strains were grouped on the basis of cluster branches which confidence was above 90% and with a maximum distance of 0.5 between isolates. In the matrix of gene content, a black colour indicates the presence of the gene (1) and a white colour indicates the absence of the gene (0). The genes on the left are ordered as in Table 1. More specifically, the different lines of the matrix correspond to the following gene markers: 1) LSA1641, 2) LSA1182 and LSA1183_c, 3) LSA0172, 4) LSA1731, 5) LSA0211 and LSA0212, 6) LSA1579 and LSA1580, 7) LSA0118, 8) LSA0529, 9) LSA0439, 10) LSA0572, 11) LSA0219b, 12) LSA0564_a, LSA0564_b and LSA0564_c, 13) FGP21-0001, 14) sspA and spiA, 15) FGP332-0001, 16) FGP332-0002, 17) FGP332-007, 18) FGP332-0008, 18) FGP332-0009, 19) FGP332-0010, 20) FGP332-0011, 21) FGP332-0011, 22) FGP332-0012, 23) FGP332-0013.

More precisely, the following correspondence between the pattern of presence or absence of the 29 marker genes defined above and 75 *L. sakei* strains has been obtained, as illustrated in FIG. 3:

- in strain DSM20019, the marker gene SEQ ID NO: 21 is present, and the other marker genes are absent.
- in strain CTC494, the marker gene SEQ ID NO: 21 is present, and the other marker genes are absent.
- in strain AGR46, the marker genes SEQ ID NO: 1, SEQ ID NO: 2, SEQ ID NO: 3, SEQ ID NO: 4, SEQ ID NO: 11, SEQ ID NO: 13, SEQ ID NO: 14, and SEQ ID NO: 24 are present and the other marker genes are absent.

TABLE 1

Correspondence between the locus tag and the name of the gene markers.

| SEQ ID NO | Locus Tag | Gene name |
| --- | --- | --- |
| 1 | LSA1641 | N-acetylmannosamine-6-phosphate 2-epimerase (N-acetylmannosamine-6-phosphate 2 epimerase)) |
| 2 | LSA1182 | Putative Cytochrome P450 (authentic frameshifted gene) C-terminal part |
| 3 | LSA1183_c | Putative Cytochrome P450 (authentic frameshifted gene) N-terminal part |
| 4 | LSA0172 | CscC-type cell-surface protein with Invasin/Mucin-like domain and WxL domain |
| 5 | LSA1731 | CscC-type cell-surface protein with Haemagluttinine-like domain and WxL domain |
| 6 | LSA0211 | CscC-type cell-surface protein with adhesion-like domain and WxL domain (authentic frameshifted gene) N-terminal part |
| 7 | LSA0212 | CscC-type cell-surface protein with adhesion-like domain and WxL domain (authentic frameshifted gene) C-terminal part |
| 8 | LSA1579 | Putative teichoic acid/polysaccharide export protein complex |
| 9 | LSA1580 | Putative teichoic acid/polysaccharide export protein complex |
| 10 | LSA0118 | Hypothetical protein (Putative cell-surface collagen-binding protein) |
| 11 | LSA0529 | MarR-type Transcriptional regulator, putative peroxide stress regulator OhrR |
| 12 | LSA0439 | Hypothetical extracellular lipase/esterase precursor |
| 13 | LSA0572 | Threonine deaminase (Threonine ammonia-lyase) |
| 14 | LSA0219_b | Putative cyanate transport protein |
| 15 | LSA0564_a | Hypothetical small peptide |
| 16 | LSA0564_b | Hypothetical small peptide |
| 17 | LSA0564_c | Putative bacteriocin Immunity protein |
| 18 | FGP21-0001 | Putative bacteriocin Immunity protein |
| 19 | sspA | Bacteriocin sakacin P precursor (Sakacin 674) |
| 20 | spiA | Sakacin P immunity protein |
| 21 | FGP332-0001 | Putative 6-phospho-beta-glucosidase |
| 22 | FGP332-0002 | CscC-type cell-surface protein with bacterial adhesion-like domain and WxL domain |
| 23 | FGP332-0007 | Putative autotransporter |
| 24 | FGP332-0008 | Hypothetical protein |
| 25 | FGP332-0009 | Hypothetical protein |
| 26 | FGP332-0010 | Hypothetical protein |
| 27 | FGP332-0011 | Putative transcriptional regulator, LysR family |
| 28 | FGP332-0012 | Putative quinine oxidoreductase |
| 29 | FGP332-0013 | Putative asparagines synthase | in strain 156, the marker genes SEQ ID NO: 1, SEQ ID NO: 2, SEQ ID NO: 3, SEQ ID NO: 4, SEQ ID NO: 11, SEQ ID NO: 13, SEQ ID NO: 14, SEQ ID NO: 15, SEQ ID NO: 16, SEQ ID NO:17 and SEQ ID NO: 24 are present and the other marker genes are absent.

in strain AGR51, the marker genes SEQ ID NO: 1, SEQ ID NO: 2, SEQ ID NO: 3, SEQ ID NO: 4, SEQ ID NO: 13, SEQ ID NO: 14, SEQ ID NO:18, SEQ ID NO: 21 and SEQ ID NO: 24 are present and the other marker genes are absent.

in strain MF1048, the marker genes SEQ ID NO: 1, SEQ ID NO: 2, SEQ ID NO: 3, SEQ ID NO: 4, SEQ ID NO: 11, SEQ ID NO: 12, SEQ ID NO:13, SEQ ID NO: 14, SEQ ID NO: 21, SEQ ID NO: 24 and SEQ ID NO: 29 are present and the other marker genes are absent.

in strain MF2092, the marker genes SEQ ID NO: 1, SEQ ID NO: 2, SEQ ID NO: 3, SEQ ID NO: 4, SEQ ID NO: 11, SEQ ID NO: 12, SEQ ID NO:13, SEQ ID NO: 14, SEQ ID NO: 21, SEQ ID NO: 24 and SEQ ID NO: 29 are present and the other marker genes are absent.

in strain 195, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 21, and SEQ ID NO: 25 are present and the other marker genes are absent.

in strain CIP105422, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 11, SEQ ID NO: 12, SEQ ID NO: 19, SEQ ID NO: 20, SEQ ID NO; 21, SEQ ID NO: 22, SEQ ID NO: 24 and SEQ ID NO: 27 are present and the other marker genes are absent.

in strain CTC429, the marker genes SEQ ID NO: 1, SEQ ID NO:2, SEQ ID NO: 3, SEQ ID NO: 4, SEQ ID NO: 5, SEQ ID NO: 8, SEQ ID NO: 9, SEQ ID NO: 11, SEQ ID NO: 12, SEQ ID NO: 19, SEQ ID NO: 20, SEQ ID NO: 21, SEQ ID NO: 22, SEQ ID NO: 23, SEQ ID NO: 24, SEQ ID NO: 26, SEQ ID NO: 27, SEQ ID NO: 28 and SEQ ID NO: 29 are present and the other marker genes are absent.

in strain LTH673, the marker genes SEQ ID NO: 1, SEQ ID NO: 2, SEQ ID NO: 3, SEQ ID NO: 4, SEQ ID NO: 11, SEQ ID NO: 12, SEQ ID NO: 19, SEQ ID NO: 20, SEQ ID NO: 21, SEQ ID NO: 22, SEQ ID NO: 25, SEQ ID NO: 26 and SEQ ID NO: 27 are present and the other marker genes are absent.

in strain 14, the marker genes SEQ ID NO: 1, SEQ ID NO: 2, SEQ ID NO: 3, SEQ ID NO: 4, SEQ ID NO: 8, SEQ ID NO: 9, SEQ ID NO: 10, SEQ ID NO: 12, SEQ ID NO: 14, SEQ ID NO: 19, SEQ ID NO: 20, SEQ ID NO: 21, SEQ ID NO: 22, SEQ ID NO: 24, SEQ ID NO: 26, SEQ ID NO: 27 and SEQ ID NO: 29 are present and the other marker genes are absent.

in strain 18, the marker genes SEQ ID NO:1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID N: 12, SEQ ID NO: 14, SEQ ID NO: 19, SEQ ID NO: 20, SEQ ID NO: 21, SEQ ID NO: 22, SEQ ID NO: 24, SEQ ID NO: 25, SEQ ID NO: 26, SEQ ID NO: 27 and SEQ ID NO: 29 are present and the other marker genes are absent.

in strain LV52, the marker genes SEQ ID NO: 1, SEQ ID NO: 2, SEQ ID NO: 3, SEQ ID NO: 4, SEQ ID NO: 10, SEQ ID NO: 11, SEQ ID NO: 12, SEQ ID NO: 14, SEQ ID NO: 19, SEQ ID NO: 20, SEQ ID NO: 21, SEQ ID NO: 22, SEQ ID NO: 26 and SEQ ID NO: 27 are present and the other marker genes are absent.

in strain LV59, the marker genes SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 14, SEQ ID NO: 19, SEQ ID NO: 20, SEQ ID NO: 21, SEQ ID NO: 22, SEQ ID NO: 25, SEQ ID NO: 26, SEQ ID NO: 27 and SEQ ID NO: 29 are present and the other marker genes are absent.

in strain LV92, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 14, SEQ ID NO: 19, SEQ ID NO: 20, SEQ ID NO: 21, SEQ ID NO: 22, SEQ ID NO: 26, SEQ ID NO: 27 and SEQ ID NO: 29 are present and the other marker genes are absent.

in strain CRL1467, the marker genes SEQ ID NO: 1, SEQ ID NO: 2, SEQ ID NO: 3, SEQ ID NO: 4, SEQ ID NO: 6, SEQ ID NO: 7, SEQ ID NO: 13, SEQ ID NO: 15, SEQ ID NO: 16, SEQ ID NO: 17, SEQ ID NO: 21, SEQ ID NO: 22, SEQ ID NO: 24 and SEQ ID NO: 28 are present and the other marker genes are absent.

in strain CTC335, the marker genes SEQ ID NO: 1, SEQ ID NO: 2, SEQ ID NO: 3, SEQ ID NO: 4, SEQ ID NO: 6, SEQ ID NO: 7, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24 and SEQ ID NO: 28 are present and the other marker genes are absent.

in strain SF842, the marker genes SEQ ID NO: 1, SEQ ID NO: 2, SEQ ID NO: 3, SEQ ID NO: 4, SEQ ID NO: 6, SEQ ID NO: 7, SEQ ID NO: 13, SEQ ID NO: 14, SEQ ID NO: 21, SEQ ID NO: 22, SEQ ID NO: 24, SEQ ID NO: 25, SEQ ID NO: 27 and SEQ ID NO: 28 are present and the other marker genes are absent.

in strain SF770, the marker genes SEQ ID NO: 1, SEQ ID NO: 2, SEQ ID NO: 3, SEQ ID NO: 4, SEQ ID NO: 6, SEQ ID NO: 7, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24, SEQ ID NO: 28 and SEQ ID NO: 29 are present and the other marker genes are absent.

in strain SF771, the marker genes SEQ ID NO: 1, SEQ ID NO: 2, SEQ ID NO: 3, SEQ ID NO: 4, SEQ ID NO: 6, SEQ ID NO: 7, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24 and SEQ ID NO: 28 are present and the other marker genes are absent.

in strain CTC287, the marker genes SEQ ID NO: 1, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 22, SEQ ID NO: 27 and SEQ ID NO: 28 are present and the other marker genes are absent.

in strain CTC041, the marker genes SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO:15, SEQ ID NO: 16, SEQ ID NO: 17, SEQ ID NO: 22, SEQ ID NO: 27 and SEQ ID NO: 28 are present and the other marker genes are absent.

in strain CTC427, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 22, SEQ ID NO: 27 and SEQ ID NO: 28 are present and the other marker genes are absent.

in strain YME344, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 27 and SEQ ID NO: 28 are present and the other marker genes are absent.

in strain V553, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17 are present and the other marker genes are absent.

in strain LV34, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID N: 15, SEQ ID NO: 16 and SEQ ID NO: 17 are present and the other marker genes are absent.

in strain 23K, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17 are present and the other marker genes are absent.

in strain 72, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17 are present and the other marker genes are absent.

in strain 504, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 28 and SEQ ID NO: 29 are present and the other marker genes are absent.

in strain TISTR911, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 28 are present and the other marker genes are absent.

in strain YMW540, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 13, SEQ ID NO: 14, SEQ ID NO: 21, SEQ ID NO: 23 and SEQ ID NO: 24 are present and the other marker genes are absent.

in strain 300, the marker genes SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21 and SEQ ID NO: 23 are present and the other marker genes are absent.

in strain LV5, the marker genes SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 21 and SEQ ID NO: 23 are present and the other marker genes are absent.

in strain LTH2070, the marker genes SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 14, SEQ ID NO: 18, SEQ ID NO: 22, SEQ ID NO: 24, SEQ ID NO: 26, SEQ ID NO: 27 and SEQ ID NO: 28 are present and the other marker genes are absent.

in strain JG3, the marker genes SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 22, SEQ ID NO: 24, SEQ ID NO: 27 and SEQ ID NO: 29 are present and the other marker genes are absent.

in strain LTH1764, the marker genes SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 22, SEQ ID NO: 24, SEQ ID NO: 27 and SEQ ID NO: 29 are present and the other marker genes are absent.

in strain CTC6626, the marker genes SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 22, SEQ ID NO: 24, SEQ ID NO: 25, SEQ ID NO: 27 and SEQ ID NO: 28 are present and the other marker genes are absent.

in strain SF841, the marker genes SEQ ID NO: 1, SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 22, SEQ ID NO: 24, SEQ ID NO: 25, SEQ ID NO: 27 and SEQ ID NO: 28 are present and the other marker genes are absent.

in strain SF843, the marker genes SEQ ID NO: 1, SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 13, SEQ ID NO: 14, SEQ ID NO: 18, SEQ ID NO: 22, SEQ ID NO: 24, SEQ ID NO: 25, SEQ ID NO: 27 and SEQ ID NO: 28 are present and the other marker genes are absent.

in strain CTC163, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 15, SEQ ID NO: 16, SEQ ID NO: 17, SEQ ID NO: 21, SEQ ID NO: 22, SEQ ID NO: 24 and SEQ ID NO: 28 are present and the other marker genes are absent.

in strain LTH5590, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 15, SEQ ID NO: 16, SEQ ID NO: 17, SEQ ID NO: 22, SEQ ID NO: 23, SEQ ID NO: 24, SEQ ID NO: 25, SEQ ID NO: 27 and SEQ ID NO: 28 are present and the other marker genes are absent.

in strain CTC014, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 25, SEQ ID NO: 27 and SEQ ID NO: 28 are present and the other marker genes are absent.

in strain 160K, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 25, SEQ ID NO: 27 and SEQ ID NO: 28 are present and the other marker genes are absent.

in strain AGR48, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 21, SEQ ID NO: 22, SEQ ID NO: 23, SEQ ID NO: 24, SEQ ID NO: 25, SEQ ID NO: 27 and SEQ ID NO: 28 are present and the other marker genes are absent.

in strain LTH5589, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 25, SEQ ID NO: 27, SEQ ID NO: 28 and SEQ ID NO: 29 are present and the other marker genes are absent.

in strain 112, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 25, SEQ ID NO: 26, SEQ ID NO: 27 and SEQ ID NO: 29 are present and the other marker genes are absent.

in strain YMH243, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24, SEQ ID NO: 25, SEQ ID NO: 26, SEQ ID NO: 27 and SEQ ID NO: 29 are present and the other marker genes are absent.

in strain 134, the marker genes SEQ ID NO: 1, SEQ ID NO: 2, SEQ ID NO: 3, SEQ ID NO: 4, SEQ ID NO: 5, SEQ ID NO: 10, SEQ ID NO: 12, SEQ ID NO: 13, SEQ ID NO: 15, SEQ ID NO: 16, SEQ ID NO: 17, SEQ ID NO: 22, SEQ ID NO: 24, SEQ ID NO: 27, SEQ ID NO: 28 and SEQ ID NO: 29 are present and the other marker genes are absent.

in strain YMW557, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 22, SEQ ID NO: 24, SEQ ID NO: 27, SEQ ID NO: 28 and SEQ ID NO: 29 are present and the other marker genes are absent.

in strain L110, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24, SEQ ID NO: 27 and SEQ ID NO: 29 are present and the other marker genes are absent.

in strain LTH5588, the marker genes SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 24, SEQ ID NO: 27 and SEQ ID NO: 29 are present and the other marker genes are absent.

in strain MF2091, the marker genes SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27, SEQ ID NO: 28 and SEQ ID NO: 29 are present and the other marker genes are absent.

in strain MF2089, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27, SEQ ID NO: 28 and SEQ ID NO: 29 are present and the other marker genes are absent.

in strain MF2090, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27 and SEQ ID NO: 29 are present and the other marker genes are absent.

in strain 745, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27 and SEQ ID NO: 29 are present and the other marker genes are absent.

in strain 710, the marker genes SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 25, SEQ ID NO: 27, SEQ ID NO: 28 and SEQ ID NO: 29 are present and the other marker genes are absent.

in strain 205, the marker genes SEQ ID NO: 1, SEQ ID NO: 2, SEQ ID NO: 3, SEQ ID NO: 4, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27 and SEQ ID NO: 28 are present and the other marker genes are absent.

in strain MF2088, the marker genes SEQ ID NO: 1, SEQ ID NO: 2, SEQ ID NO: 3, SEQ ID NO: 4, SEQ ID NO:

5, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 21, SEQ ID NO: 22, SEQ ID NO: 23, SEQ ID NO: 24, SEQ ID NO: 27 and SEQ ID NO: 28 are present and the other marker genes are absent.

in strain CTC494, the marker genes SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 22, SEQ ID NO: 24, SEQ ID NO: 27 and SEQ ID NO: 28 are present and the other marker genes are absent.

in strain 331, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 22, SEQ ID NO: 23, SEQ ID NO: 24 and SEQ ID NO: 27 are present and the other marker genes are absent.

in strain AGR53, the marker genes SEQ ID NO: 1, SEQ ID NO: 2, SEQ ID NO: 3, SEQ ID NO: 4, SEQ ID NO: 6, SEQ ID NO: 7, SEQ ID NO: 11, SEQ ID NO: 12, SEQ ID NO: 13, SEQ ID NO: 22, SEQ ID NO: 24 and SEQ ID NO: 27 are present and the other marker genes are absent.

in strain 495, the marker genes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 21, SEQ ID NO: 22, SEQ ID NO: 24, SEQ ID NO: 27 and SEQ ID NO: 28 are present and the other marker genes are absent.

in strain Lb706, the marker genes SEQ ID NO: 1, SEQ ID NO: 2, SEQ ID NO: 3, SEQ ID NO: 4, SEQ ID NO: 5, SEQ ID NO: 11, SEQ ID NO: 13, SEQ ID NO: 22, SEQ ID NO: 24, SEQ ID NO: 27, SEQ ID NO: 28 and SEQ ID NO: 29 are present and the other marker genes are absent.

in strain LV21, the marker genes SEQ ID NO: 1, SEQ ID NO: 2, SEQ ID NO: 3, SEQ ID NO: 4, SEQ ID NO: 5, SEQ ID NO: 11, SEQ ID NO: 13, SEQ ID NO: 22, SEQ ID NO: 24, SEQ ID NO: 27, SEQ ID NO: 28 and SEQ ID NO: 29 are present and the other marker genes are absent.

in strain LTH677, the marker genes SEQ ID NO: 5, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID N: 17, SEQ ID NO: 18, SEQ ID NO: 21, SEQ ID NO: 22, SEQ ID NO: 23, SEQ ID NO: 24, SEQ ID NO: 27, SEQ ID NO: 28 and SEQ ID NO: 29 are present and the other marker genes are absent.

in strain 332, the marker genes SEQ ID NO: 1, SEQ ID NO: 4, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID N: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29 are present and the other marker genes are absent.

in strain 33, the marker genes SEQ ID NO: 6, SEQ ID NO: 7, SEQ ID NO: 8, SEQ ID NO: 9, SEQ ID NO: 13, SEQ ID NO: 18, SEQ ID NO: 22, SEQ ID NO: 24, SEQ ID NO: 27 and SEQ ID NO: 28 are present and the other marker genes are absent.

in strain 64, the marker genes SEQ ID NO: 6, SEQ ID NO: 7, SEQ ID NO: 10, SEQ ID NO: 13, SEQ ID NO: 18, SEQ ID NO: 21, SEQ ID NO: 22, SEQ ID NO: 23, SEQ ID NO: 24, SEQ ID NO: 27 and SEQ ID NO: 28 are present and the other marker genes are absent.

in strain CTC6469, the marker genes SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 18, SEQ ID NO: 21, SEQ ID NO: 22, SEQ ID NO: 24 and SEQ ID NO: 27 are present and the other marker genes are absent.

in strain LTH5728, the marker genes SEQ ID NO: 5, SEQ ID NO: 6, SEQ ID NO: 7, SEQ ID NO: 8, SEQ ID NO: 9, SEQ ID NO: 10, SEQ ID NO: 13, SEQ ID NO: 14, SEQ ID NO: 18, SEQ ID NO: 21, SEQ ID NO: 22, SEQ ID NO: 23, SEQ ID NO: 24 and SEQ ID NO: 27 are present and the other marker genes are absent.

in strain 21, the marker genes SEQ ID NO: 1, SEQ ID NO: 2, SEQ ID NO: 3, SEQ ID NO: 5, SEQ ID NO: 6, SEQ ID NO: 7, SEQ ID NO: 13, SEQ ID NO: 14, SEQ ID NO: 18, SEQ ID NO: 22 and SEQ ID NO: 24 are present and the other marker genes are absent.

in strain TISTR890, the marker genes SEQ ID NO: 5, SEQ ID NO: 6, SEQ ID NO: 7, SEQ ID NO: 13, SEQ ID NO: 18, SEQ ID NO: 21, SEQ ID NO: 24 and SEQ ID NO: 28 are present and the other marker genes are absent.

in strain ATCC15521, the marker genes SEQ ID NO: 6, SEQ ID NO: 7, SEQ ID NO: 13, SEQ ID NO: 14, SEQ ID NO: 18, SEQ ID NO: 21 and SEQ ID NO: 24 are present and the other marker genes are absent.

in strain LTH675, the marker genes SEQ ID NO: 6, SEQ ID NO: 7, SEQ ID NO: 13, SEQ ID NO: 14, SEQ ID NO: 18, SEQ ID NO: 21 and SEQ ID NO: 23 are present and the other marker genes are absent.

The present invention also relates to a method for characterizing a *L. sakei* strain which comprises the step consisting of determining the presence or absence of at least one marker gene selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29) in said *L. sakei* strain.

Numerous methods allowing determining the presence or absence of a gene in a bacterial strain are well known from one skilled in the art. These methods include, without being limited, the use of an antibody specifically binding to an antigen which is constituted by the expression product of said marker gene(s), the detection of mRNA, cDNA or polypeptide from said marker gene(s), or of fragments thereof. Preferably, the presence or absence of said marker gene(s) is determined according to the invention by amplification, or by hybridization with DNA probes specific of said marker gene(s).

More preferably, the presence or absence of all of said marker genes SEQ ID NO:1 to SEQ ID NO:29 is determined.

In a particular embodiment, the combination of probes of these marker genes is assembled on a same support, preferably a standardized support. These supports are known from one skilled in the art. Their size can vary according to the apparatuses used to detect the presence or absence of said marker gene(s).

Advantageously, the combination of marker genes according to the invention is in form of a DNA matrix, comprising a support on which nucleic acids fragments likely to hybridize to target genes are deposed, preferably in a standardized way. The size of such supports varies according to the preparation and detection methods used. Such small supports are also referred to DNA array.

Another aspect of the present invention thus concerns a DNA array which comprises a combination of markers as defined above.

As used herein, the term "DNA array" refers to a set of genes, fragment of genes, oligonucleotides deposited on a support (glass slide, nylon membrane . . . ) with a high density. Numerous scientific publications about the preparation and the use of DNA arrays are available.

In another aspect of the invention, a classification of said *L. sakei* strain is performed by analyzing the pattern of presence or absence of the above marker gene(s) and calculating a Jaccard index or Dice coefficient or any binary distance matrix with regard to a set of reference *L. sakei* strains. The Jaccard index can be calculated as described in Jaccard P, 1901 (Jaccard P., Bulletin de la Societe Vaudoise des Sciences Naturelles, 37:241-272). The Dice coefficient can be calculated as described by Van Rijsbergen, 1979 (Van Rijsbergen, 1979, Information Retrieval, London: Butterworths).

As used herein, the term "classification" refers to organizing the strains in different subfamilies according to their genetic pattern. In particular, strains that display the same pattern of genes belong to the same subfamily.

As used herein, the term "reference *L. sakei* strains" refers to a set or collection of *L. sakei* strains in which the presence or absence of said marker gene(s) has already been determined according to the invention and to which said *L. sakei* strain to be classified is compared. Namely said reference *L. sakei* strains were used to constitute subfamilies or clusters of *L. sakei* strains in which said *L. sakei* strain to be classified is intended to be positioned.

Preferably, the set of reference *L. sakei* strains according to the invention comprises the strains disclosed in Table 2. Nevertheless, other known *L. sakei* strains can be used as reference strains, and are well known from one skilled in the art.

Preferably, said subfamilies of *L. sakei* strains constituted by said reference *L. sakei* strains are as defined in Example 3. However, one skilled in the art knows that clustering can evolve according to the identification of new strains. Accordingly, the use of the method according to the present invention to classify *L. sakei* strains in clusters which are not specifically described herein is under the scope of the present invention.

As used herein, the term "Jaccard index" is a statistic used for comparing the similarity and diversity of sample sets. The Jacquard index is defined as the size of the intersection divided by the size of the union of the sample sets, according to the following formula: $J(A,B)=|A \cap B|/|A \cup B|$.

Preferably, calculating of the Jaccard Index according to the invention is performed via the software R (R Development Core Team, 2006 R: A language and environment for statistical computing. Vienna, Austria. R Foundation for Statistical Computing) which eventually provides a clustering tree displaying the location of said *L. sakei* strain among the different subfamilies of reference *L. sakei* strains.

As used herein the term "Dice coefficient" is a similarity measure related to the Jaccard index. The Dice coefficient is similar to Jaccard index but gives twice the weight to agreements according to the formula $s=2|A \cap B|/(|A|+|B|)$.

Another aspect of the present invention concerns a method of comparing at least two *L. sakei* strains comprising the steps consisting of:
  a) determining the presence or absence of at least one marker gene selected from the group consisting of LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29), in a first *L. sakei* strain, and
  b) determining the presence or absence of said at least one marker gene in a second *L. sakei* strain, as defined above wherein, if the pattern of presence or absence of said at least one marker gene is different between said first and said second *L. sakei* strains, then the *L. sakei* strains are different.

Preferably, in the above method of comparing at least two *L. sakei* strains, the presence or absence of all of said marker genes SEQ ID NO:1 to SEQ ID NO:29 is determined.

In particular, the above method of comparing at least two *L. sakei* strains further comprises the step of analysing the pattern of presence or absence of said marker genes by calculating a Jaccard index, a Dice coefficient or any binary distance matrix as defined above.

The above defined methods according to the present invention are of particular interest to identify *L. sakei* strains in a cocktail of strains that can be used as biopreservative on meat and/or fish. Another issue of characterizing such cocktail of strains is to quantify each strain present in said cocktail.

Accordingly, another aspect of the present invention relates to a method of quantifying a specific *L. sakei* strain in a sample, which comprises the steps consisting of:
  a) identifying and/or characterizing the *L. sakei* strains present in said sample by a method as defined above,
  b) determining the marker gene(s) which is(are) differently present in said specific *L. sakei* strain with respect to other strains present in said sample, and
  c) amplifying said gene(s) by quantitative PCR.

Methods of quantitative PCR are well-known in the art and include real-time PCR, competitive PCR and radioactive PCR.

As used herein the term "sample" encompasses samples in which one or several *L. sakei* strain(s) is/are present, optionally in combination with other bacterial species.

Accordingly, the above method of quantifying a specific *L. sakei* strain in a sample may include a prior step of individualizing said strain from other strains present in the sample.

The following examples further describe the way the present inventors have identified said marker genes. These examples are illustrative, without being limited, of the above defined methods.

EXAMPLES

Example 1

Detection and Analysis of Genomic Islands in *Lactobacillus sakei* 23K Chromosome This example describes the identification by the inventors of genomic islands in *L. sakei* 23K chromosome, which carry the genes used as markers in the present invention.

It is admitted that bacterial chromosomes are divided into two sets of genes: the core gene pool, that comprises genes that persisted in the species for long enough to show maintenance among strains, and the flexible gene pool, that comprises variable and auxiliary genes generally clustered in islands and often acquired by horizontal gene transfer (HGT).

The aim of the present study is therefore to identify the putative variable genomic islands in the genome of *L. sakei* 23K and to characterize the cellular functions, estimated to be ecologically important, that could be ascribed to HGT.

Experimental Procedures
Codon Usage Analysis

The codon usage signature of highly expressed genes was searched by using the CAI introduced by Sharp and Weng-Hsiung (Sharp and Weng-Hsiung 1987 *Nucleic Acids Res.* 15:1281-1295). The codon frequencies used as a reference for CAI computation were estimated on the genes encoding ribosomal proteins and aminoacyl-tRNA synthetases found in the *L. sakei* 23K genome. Secondly, unsupervised clustering of the coding sequences (CDSs) was performed on the basis of their usage of the synonymous codons with an algorithm designed by the inventors. This approach is based on the use of a mixture model that accounts for the choice of synonymous codons in different gene classes. Briefly, once the number of gene classes is defined by the user, the model is fitted to the sequences using an iterative algorithm and the final clustering associates each CDS to its most probable class.

Here follows a more formal description of the mixture models and of the clustering procedure: let n denote the number of codon usage class, or component, of the mixture model. Each class u is characterized by its incidence in the mixture $q_u$ and a set probabilities ($f_{u,i,j}$), $1 \leq i \leq 20$, $1 \leq j \leq s_i$ where $f_{u,i,j}$ corresponds to the probability of using the jth synonymous codon for amino acid i and $s_i$ denotes the number of synonymous codon for amino acid i. Maximum Likelihood estimates of the model parameters $q_u$ and $f_{u,i,j}$ are obtained using the Expectation-Maximization algorithm. Finally, the final clustering is obtained after computing the probability of each class u for each CDS k with Bayes' formula: $p_k(u)$ is proportional to $q_u \prod f_{u,i,j}^{c(k,i,j)}$ where $p_k(u)$ denotes the probability that CDS k belongs to class u and c(k,i,j) counts the occurrences of the jth synonymous codon for amino-acid i in CDS k. A detailed presentation of the mixture model framework can be found in McLachlan and Peel (McLachlan and Peel 2000 In *Finite mixture models*. New York: Wiley-Interscience). Finally, a correspondence analysis was performed to allow the graphical display of the cloud of CDSs in a similar way as described in Médigue et al., 1991 (Médigue et al., 1991 *J. Mol. Biol.* 222:851-856). Short CDSs (less than 300 bps-100 aa long) and the two cysteine codons were omitted from the correspondence analysis as they do not allow accurate estimation of the associated relative codon frequencies. In addition, codon frequency estimates were smoothed by adding a pseudo-count 1 to all counts.

All analysis were performed with an ad-hoc Perl script named CODONUSAGE.PL responsible for computing A+T-content and CAI and also for calling both a C++ program that performs the new cluster analysis described above and a R script that performs the correspondence analysis with the CA function of the MULTIV package (R Development Core Team 2006 R: A language and environment for statistical computing. Vienne, Austria: R Foundation for Statistical Computing). All programs can be downloaded at URL: http://genome.jouy.inra.fr/~pnicolas/codonmixture/.

Results

*L. sakei* Codon Usage is Shaped by Chromosome Replication and Translation Efficiency In order to detect possible HGT events, an array of statistical measurements was used to characterize the compositional trends of the *L. sakei* 23K gene pool including G+C content analysis, Codon Adaptation Index (CAI) computations, correspondence analysis of synonymous codon usage and unsupervised clustering of the gene pool with a new method based on a mixture modelling of the usage of synonymous codons as described above.

Unsupervised clustering of the complete gene pool allowed identifying four groups of genes. Genes of the first and second groups account for 74.5% of the total gene pool. They are highly preferentially located on the leading strand of chromosome replication (93%) and are distinguished by their expression level as measured with the CAI (reflecting the protein expression level): group 1 genes have low or average CAI values whereas group 2 genes show high CAI values. This last group comprises typical highly expressed genes such as S-layer-like proteins, Cpl-like chaperones and highly expressed metabolically important enzymes such as those of the glycolytic pathway. Group 3 encompasses 18.5% of the total gene pool and contains mostly genes located on the lagging strand (87%).

Therefore, three groups of genes whose codon usage are strongly shaped by their orientation relative to the chromosome replication and by their putative level of translation efficiency were able to be revealed.

More importantly, the models allowed demarcating a fourth group of genes (7% of the total gene pool) with atypical A+T-rich content and low CAI value. The compositional pattern of this fourth group may have been shaped by HGT as genes with low G+C-content have been described to be related to HGT in many bacteria (Médigue al., 1991 *J. Mol. Biol.* 222:851-856).

Atypical A+T-Rich *L. sakei* 23K Genes are Clustered in Genomic Islands.

To verify the HGT-related origin of this fourth group of genes, their corresponding genetic context in the chromosome was further looked at in more details. It was presently first noticed that most of these atypical CDSs are grouped to form large islands of functionally related genes often located nearby mobile elements, a classical feature of horizontally transferred genetic clusters (Ochman et al., 2000 *Nature* 405: 299-304).

Furthermore, genes with atypical codon usage were often encoding products homologous to proteins only found in phylogenetic distant bacterial genera.

From these data, the inventors demonstrated that the putative HGT gene pool was thus comprised of 27 genomic islands (from 1.6 to 28 kb with an average size of 7.3 kb) and of 49 single genes, covering altogether 235 kb (12.5%) of *L. sakei* 23K chromosome. It has also been assumed that the 27 genomic islands may pertain to the dispensable *L. sakei* 23K genome.

Example 2

Intra-Species Genomic Diversity and Natural Population Structure of the Meat-Borne Lactic Acid Bacterium *Lactobacillus sakei*

This example describes the classification, by the inventors, of *L. sakei* strains using marker genes.

In this study, the inventors have performed a combination of several typing techniques including pulse-field gel electrophoresis (PFGE) genome mapping, PCR-based detection of genetic markers taken from a pool of variable genes identified by the inventors (see example 1) for hierarchical clustering of the strains, and finally, a proteomic comparison to evaluate their respective phenotypic diversity. Isolates from diverse laboratory collections corresponding to various geographical locations and to various sources of meat- or fish-related products have been specifically chosen, based on the expectation that these undomesticated strains would represent the diversity of the natural *L. sakei* population.

These results provide an integrated genomic-based framework for classifying the repertoire of molecular subtypes of *L. sakei* isolates.

Experimental Procedures

Bacterial Strains and Culture Conditions

All *L. sakei* and *L. curvatus* strains used in this study are described in Table 2. Bacterial strains were grown to midlog exponentional phase in MRS broth medium (Difco) (De man et al., 1960 *J. Appl. Bacteriol.* 23:133-135) at 30° C. For proteomic studies, bacterial strains were grown at 30° C. in chemically defined medium MCD (Lauret et al., 1996 *Appl Environ Microbiol.* 62:1922-1927) supplemented with 0.5% glucose.

Molecular Biology Techniques

Substrative suppressive hybridization (HSS) of *L. sakei* 332F was performed as follows: to prepare tester strain 332F, cured from its endogenous plasmid pRV500 (Alpert et al., 2003 *Appl Environ Microbiol.* 69:5574-5584), the parent *L. sakei* 332 was electroporated by the method of Berthier et al., (Berthier et al., 1996 *Appl. Envir. Microbiol.* 62:3037-3041) with pRV566 plasmid carrying resistance to erythromycin and derived from pRV500 replicon (Alpert et al., 2003 *Appl. Envir. Microbiol.* 69:5574-5584).

One Erythromycin resistant clone was further cultivated for 200 generations in MRS broth without antibiotic at 30° C. Several dilutions from the last culture were plated on MRS agar. Replica plating of 200 clones on MRS agar with or without erythromycin (5 µg/ml) allowed selecting one erythromycin sensitive clone. The loss of pR566 plasmid was verified by Southern blotting (ECL™ direct nucleic acid labelling, Amersham Biosciences) using a probe specific of the repA gene. The corresponding strain was named 332F.

HSS experiment was carried out with Clontech PCR-selected™ bacterial genome subtraction kit according to the manufacturer recommendations and by using *L. sakei* 23K as driver. This technique led to the identification of 8 new genes absent from *L. sakei* 23K. FGP21-0001 gene from *L. sakei* 21 was identified after sequencing of a PCR product (LSA0565 to LSA566) giving an unexpected size and revealing a new type of bacteriocin immunity-like protein-encoding gene.

TABLE 2

*L. sakei* and *L. curvatus* strains used in this study.

| Laboratory Collection - Country | Number of strains | Names (synonyms) | Isolated from | Reference |
|---|---|---|---|---|
| PART 1: *L. sakei* strains | | | | |
| INRA - Jouy en Josas - FRANCE Unité Flore Lactique & Environnement carné | 12 | 23K, 14, 18, 21, 33, 64, 72, 112, 134, 156 | Various French-style fermented dry sausages | Berthier et al., 1999 *Int. J. Syst. Bacteriol.* 49: 997-1007 |
| | | 160K | Fresh horse meat | Berthier et al., 1999 *Int. J. Syst. Bacteriol.* 49: 997-1007 |
| | | JG3 | Fresh beef meat | Berthier et al., 1999 *Int. J. Syst. Bacteriol.* 49: 997-1007 |
| INRA - Theix - France Station de Recherches sur la Viande | 11 | 195, 205, 300, 332 | Vacuum-packed beef meat | Champomier et al., 1987 *Ann Inst Pasteur Microbiol.* 138: 751-758 |
| | | 331, 495, 504, 532, 710, 741 | Vacuum-packed pork meat | Montel et al., 1991 *J Appl Bacteriol* 70: 469-472 |
| | | L110 | Starter for French-style fermented dry sausage | Champomier et al., 1987 *Ann Inst Pasteur Microbiol.* 138: 751-758 |
| IFREMER - Nantes - France Laboratoire de Génie Alimentaire | 5 | SF770, SF771, SF841, SF842, SF843 | Smoked salmon | Joffraud et al., 2006 *Int. J. Food Microbiol.* 112: 51-61 |
| IRTA - Monells - SPAIN Meat Technology Center | 10 | CTC014, CTC041, CTC163, CTC287, CTC335, CTC427, CTC429, CTC494, CTC6469, CTC6626 | Various Spanish-style fermented dry sausages (including Chorizo) | Hugas et al., 1995 *J. Appl. Bacteriol.* 79: 332-330 Hugas et al., 1993 *Int J Food Microbiol* 18: 107-113 |
| ARC - Langford, Bristol - UNITED KINGDOM Meat Research Institute | 6 | LV5, LV21, LV92 | Vacuum-packed pork meat - bacon | Shaw et al., 1984 *J Appl Bacteriol* 56: 25-40 |
| | | LV52, LV59 | Vacuum-packed lamb meat | Shaw et al., 1984 *J Appl Bacteriol* 56: 25-40 |
| | | LV34 | Vacuum-packed beef meat | Shaw et al., 1984 *J Appl Bacteriol* 56: 25-40 |

TABLE 2-continued

L. sakei and L. curvatus strains used in this study.

| Laboratory Collection - Country | Number of strains | Names (synonyms) | Isolated from | Reference |
|---|---|---|---|---|
| AgResearch - Hamilton - NEW ZEALAND Meat Science Group | 4 | AGR46, AGR48, AGR51, AGR53 | Chilled lamb meat | This study |
| Mahidol University - Bangkok - THAILAND Faculty of Science | 2 | TISTR890, TISTR911 | Nham (Thai-style fermented pork sausage) | Tanasupawat et al., 1983 *J. Gen. Appl. Microbiol.* 29: 487: 506 Noonpakdee et al., 1996 *Asia Pacific J. Mol. Biol. Biotechnol.* 4: 229-235 |
| Universität Hohenheim - GERMANY Institüt für Libbensmitteltechnologie | 9 | LTH673, LTH675, LTH677, LTH5728 | Various German-style fermented moist-type sausages | Vogel et al., 1991 *FEMS Microbiol Lett* 68: 183-190 |
| | | LTH1764, LTH2070 | Sauerkraut | Vogel et al., 1993 *J Appl Bacteriol* 74: 295-300 |
| | | LTH5588, LTH5589, LTH5590 | Human feces | Walter et al., 2001 *Appl. Envir. Microbiol.* 67: 2578-2585. |
| Universität Berlin - GERMANY Institute of Meat Hygiene & Technology | 1 | CIP105422$^T$ (CCUG31331) | Raw German-style sausage | Klein et al., 1996 *Int. J. Sys. Bacteriol.* 46: 367-376 |
| Kulmbach - GERMANY Federal Centre for Meat Research | 1 | Lb706 | Fresh beef meat | Schillinger et al., 1987 *Food Microbiol.* 4: 199-208 |
| MATFORSK - Ås - NORWAY Norwegian Food Research Institute | 6 | MF1048, MF2091, MF2092 MF2088, MF2089, MF209 | Smoked salmon Rakfisk (Scandinavian fermented trout) | This study This study |
| CONICET - Tucumán - ARGENTINA Centra de Referencia para Lactobacilos (CERELA) | 1 | CRL1467 | Argentinean-style fermented dry sausage | Fontana et al., 2005 *J Microbiol Methods* 63: 254-263 |
| American Type Culture Collection (Original isolate from JAPAN) | 1 | ATCC15521$^T$ (DSM20017) | Spoiled moto for Saké manufacture | Katagiri et al., 1934 *Bull. Agr. Chem. Soc. Jpn.* 10: 156-157 |
| University of Tokyo - JAPAN National Institute of Health | 5 | YMN243, YME344, YMN540, YMN557, V553 | Various fresh meat products | Morishita et al., 1986 *Int. J. Food Microbiol.* 3: 19-29 |

Part 2: *L. curvatus* strains

| | | | | |
|---|---|---|---|---|
| American Type Culture Collection (Original isolate from GERMANY) | 1 | ATCC25601$^T$ (DSM20019) | Milk | Torriani et al., 1996 |
| IRTA - Monells - SPAIN Meat Technology Centre | 1 | CTC424 | Spanish-style fermented dry sausage | Hugas et al., 1993 *Int J Food Microbiol* 18: 107-113 |

PCR-Based Detection of Genes

The presence or absence of the flexible gene pool identified by the inventors was investigated using conventional PCR-based detection and verification of genomic islands for strain clustering as follows:

PCR template was 100 ng of chromosomal DNA extracted from the 73 *L. sakei* strains and from the 2 *L. curvatus* strains. Experiments were conducted twice to confirm the negative results. In case of weak or spurious amplifications, PCR products were sequenced to check nucleotide polymorphism between strains. If necessary, primers were redesigned.

Extraction of chromosomal DNA from *L. sakei* and *L. curvatus* was performed by the method of Anderson & McKay (Anderson and McKay, 1983 *Appl Environ Microbiol*. 46:549-552). For each PCR amplification, the pair of primers was designed so that the expected length of the products was less than 2 kb.

The PCR cycling conditions were 94° C. for 4 min followed by 30 cycles of 94° C. for 1 min, 55° C. for 1 min and 72° C. for 3 min. All PCR products were examined using 1% agarose gels and stained with ethidium bromide. To confirm the truncation of some genes or the products of unexpected sizes, 10 μl of the amplicons were treated with 0.1 unit of Shrimp alkaline phosphatase (USB corporation) and 1 U of exonuclease I (*E. coli*) (Biolabs) in 20 mM Tris-HCl pH 8.0, 10 mM $MgCl_2$ buffer for 1 hour at 37° C., followed by 10 min inactivation at 94° C. The products were then sequenced using standard technology (http://www.the-mwg.com).

PFGE Experiments and I-CeuI Pattern Analysis.

Pulse-field gel electrophoresis and I-CeuI digestion pattern analysis were carried out as described by Dudez et al., 2002 (Dudez et al., 2002 *Microbiology*. 148:421-31). An average of 4 gels was performed for each strain. The distribution of the strains according to their genome size was examined using the HIST function and the probability DENSITY function of the R statistical package (R Development Core Team 2006 R: A language and environment for statistical computing. Vienna, Austria: R Foundation for Statistical Computing). A Gaussian probability distribution and a smoothing bandwidth of 30 (average standard deviation of genome size estimation) were chosen for the analyses.

Clustering of Strains.

The gene contents of the strains tested were described by using a two-character matrix (genes×isolates) with 0 for absence and 1 for presence of a gene. Genes truncated by IS elements were considered as distinct genetic identities than their wild-type counterpart. Similarities between the strains were determined using the Jaccard's correlation coefficient (Jaccard P., 1901 Bulletin de la Societe Vaudoise des Sciences Naturelles, 37:241-272). The unsupervised hierarchical clustering was performed using the complete linkage on the similarity matrix. The following functions : DIST, HCLUST and DENDROGRAM of the R statistical package (R Development Core Team 2006 R: A language and environment for statistical computing. Vienna, Austria: R Foundation for Statistical Computing) were used to generate the clustering dendrogram. The R package PVCLUST (Suzuki and Shimodeira, 2006 *Bioinformatics*. 22:1540-1542) was used for multiscale bootstrap resampling to assess the statistical stability of each node. The number of bootstrap replicates was 1,000. Approximately unbiased P-values ≧90% and Jaccard's similarity coefficient ≧50% were used to discriminate the possible strain clusters.

2D Gel Electrophoresis and Identification of Proteins by Peptide Mass Fingerprinting.

Bacterial-extract preparation, electrophoresis were performed by standard methods (Jofré et al., 2007 *Res. Microbiol.* 158:512-520). Gels were analyzed by Image Master software (Amersham Pharmacia Biotech). Spots were excised from Coomassie-stained gels as described by Marceau et al., (Marceau et al., 2004 *Appl Environ Microbiol.* 70:7260-7268) and Mass spectrometry analyses were performed as previously described by Guillot et al., (Guillot et al., 2000 *Int J Food Microbiol.* 55:47-51). MS-Fit (University of California San Francisco Mass Spectrometry Facility; http://prospector.ucsf.edu) and Mascot (Matrix Science Inc., Boston, Mass.; http://www.matrixscience.com/search_form_select.html), installed on a local server, were used to identify proteins from peptide mass fingerprints. All searches were performed against the *L. sakei* 23K database (http://www.migale.jouy.inra.fr/sakei).

Results

Selection of *L. sakei* Strains.

To carefully estimate the biodiversity of the natural *L. sakei* population, the inventors took care to analyse strains which were isolated from a variety of meat- or fish-related food products (raw or fermented) or from other sources including Sauerkraut and Human faeces. In addition, since a possible sampling bias might exist in single laboratory bacterial collections because of the isolation procedure used or the type of food materials analyzed, the *L. sakei* strains were selected from 14 different laboratory collections geographically scattered within Europe, Asia and New-Zealand. A total of 73 *L. sakei* strains were selected and analysed (Table 2) as well as two *Lactobacillus curvatus* strains, a close relative to *L. sakei* species taken as external species reference (outgroup reference).

Identification of the Main *L. sakei* Molecular Subtypes by PCR-Based Detection of the Flexible Gene Pool.

In example 1 describing an in silico analysis of *L. sakei* 23K chromosome, the inventors identified its putative flexible gene pool comprising 27 genomic islands and 49 independent genes. They decided to check the presence or absence of this pool of gene (assumed to be variable between strains) for clustering analysis of the *L. sakei* isolates and by using conventional PCR.

This strategy was first tested on a preliminary PCR experiments on a set of 20 strains to demonstrate the intra-species variation of these genes. Only 5 islands revealed to be highly conserved and were therefore removed from the analysis. To avoid clustering disturbance due to the highly laterally transferable mobile elements (Insertion sequences, phage and Restriction/modification systems), these genes were also discarded from the analysis. Furthermore, the inventors showed that most genes inside each genomic island were usually displaying similar patterns of variations (the whole island is usually present or absent). Therefore, to avoid a bias from the large genomic clusters (containing more genes than the smaller ones), a selection of maximum 4 genes (those eventually showing a different pattern of variation) were taken for each cluster.

In addition, 11 chromosomally-encoded genes from other *L. sakei* strains that were absent from *L. sakei* 23K chromosome, were incorporated in the analysis. These genes were partly chosen from previously published clusters and partly taken from partial genome sequencing of other *L. sakei* strains. This selection resulted thus in ~80% of genes originated from *L. sakei* 23K (representing 21 genomic islands and 4 independent genes) and ~20% of genes from other strains. The characteristics of these 60 genes are summarized in Tables 3 and 4

Figure 1:
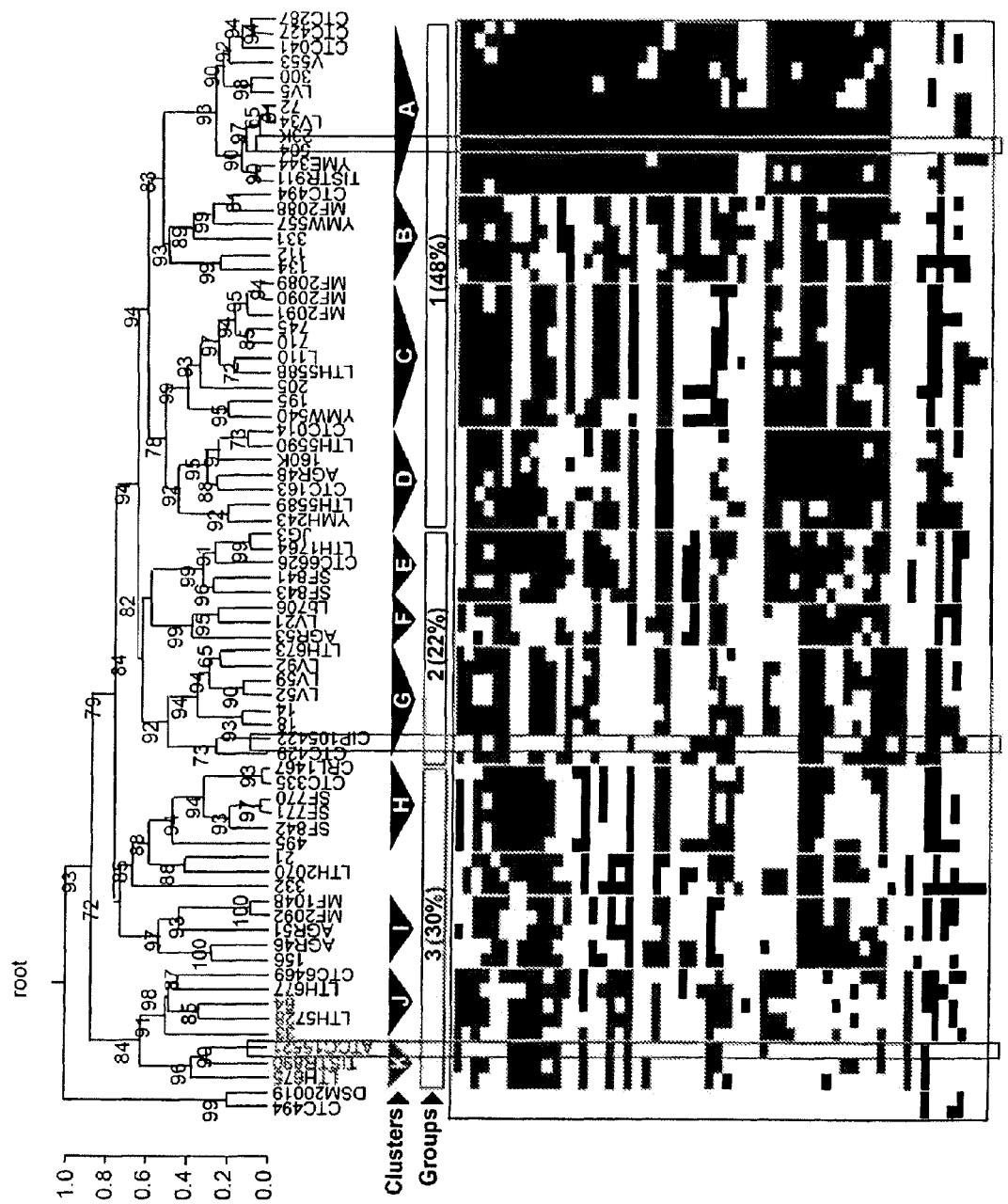
FIG. 1: *L. sakei* genomic diversity. Distribution of the 60 genetic markers among the 73 *L. sakei* isolates and the 2 *L. curvatus* isolates taken as outgroup reference. Genes are ordered on the left of the table by their position in the 23K chromosome, i.e. LSA0088, LSA0118, LSA0157, LSA0165, LSA0172, LSA0178, LSA0212, LSA0216, LSA0217, LSA0218, LSA0219_b, LSA0306, LSA0439, LSA509, LSA510, LSA0530, LSA0564_ac, LSA0565, LSA0567, LSA0572, LSA724, LSA727, LSA1006, LSA1182/3, LSA1220, LSA1222, LSA1227, LSA1232, LSA1283, LSA1509, LSA1510, LSA1512, LSA1510_a, LSA1510_g, LSA1572, LSA1579/80, LSA1581, LSA1584, LSA1641, LSA1640, LSA1640, LSA1720, LSA1724, LSA1730, LSA1731, LSA1806, LSA1809, LSA1874, sspT, sspA, FGP21-0001, DrsA, FGP332-0001, FGP332-0002, FGP332-0003, FGP332-0006, FGP332-0005, lacC, lacG. Colours: white, absent; black, present. The dendrogram showing estimates of genomic relationships of the strains was constructed by complete linkage hierarchical analysis. The scale represents the distance at each node. A coefficient of 1 would denote complete independence, and zero would indicate absolute identity. P-values at node indicate confidence of the clustering by multiscale bootstrap resampling using the PvCLUST program. Strains were grouped on the basis of cluster branches which confidence was above 90% and with a maximum distance of 0.5 between isolates. Main groups of strains are indicated with their respective percentage of the total population. The subspecies type strains and the reference strain *L. sakei* 23K are indicated by vertical rectangle.

Based on the PCR analysis of the 60 genes, the inventors attempted to classify the *L. sakei* natural isolates by using unsupervised complete-linkage hierarchical clustering algorithm and by estimating P-values via multiscale bootstrap resampling to assess the uncertainty of the clustering analysis (FIG. 1). From the resulting dendrogram, at least 11 bootstrap-supported clusters of strains divided in three main groups were clearly identified by the inventors.

Cluster A comprises the reference strain 23K and clusters B to D comprise strains closely related to this cluster forming together group 1. The other groups represent clusters of strains which are hierarchically less related to group 1 and comprise the *L. sakei* subsp. *carnosus* type strain CIP 105422T (cluster G, group 2) and the *L. sakei* subsp. *sakei* type strain ATCC 15521T (cluster K, group 3), the latter being the most distantly related to group 1. Three strains (332, 21 and LTH2070) from group 3 could not be clustered with certainty between cluster H and cluster I.

Variations of Chromosome Size and Geometry Between *L. sakei* Genotypic Clusters.

The inventors then investigated the extent of genome size variation between *L. sakei* isolates by PFGE analysis of I-CeuI-digested fragments. I-CeuI-mapping of *L. sakei* chromosome is resulting in seven DNA fragments (Dudez et al., 2002 *Microbiology*. 148:421-31) of various size and is an efficient tool in resolving overall genome size and geometry between *L. sakei* strains.

Figure 2A:
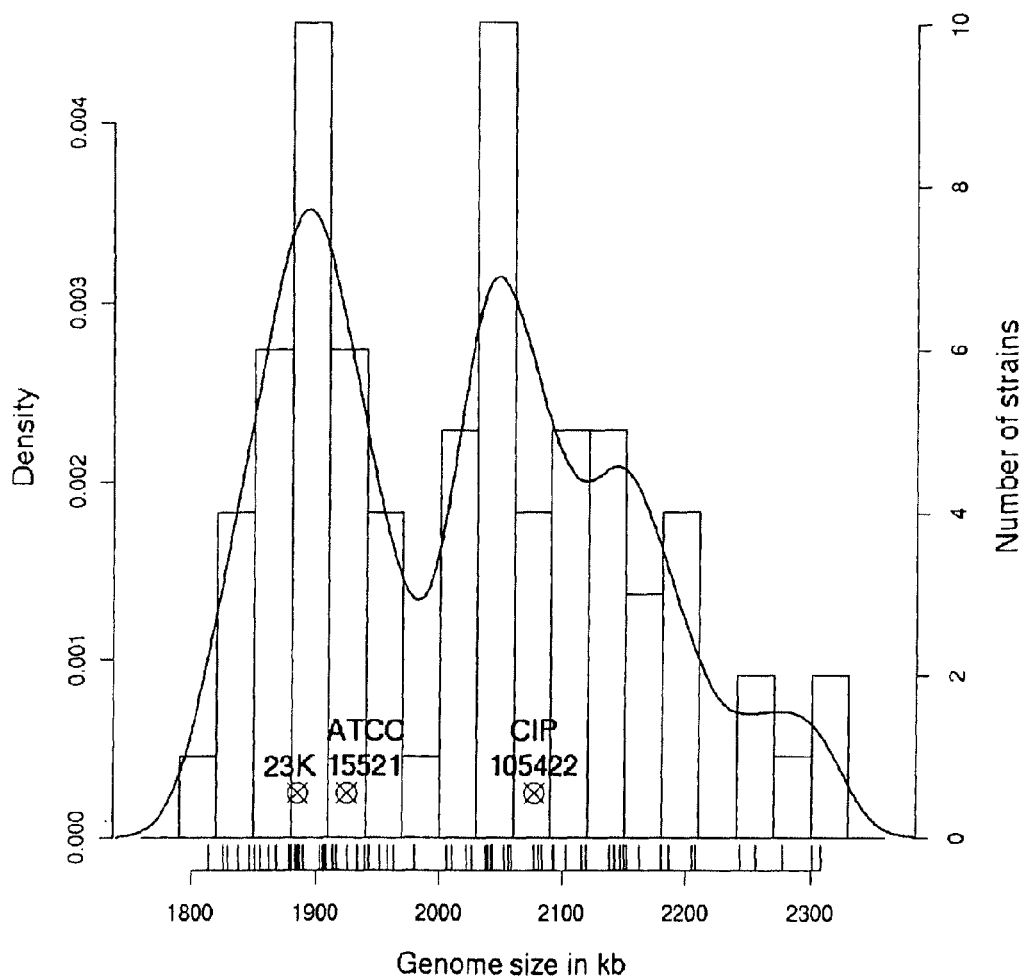
FIG. 2: (A) Histogram distribution of genome size among *L. sakei* isolates. Strains are represented by rug bars above the genome size axis. Histogram bars are representing the number of strains within a genome size window of 30 kb (average standard deviation of PFGE measurements). The Gaussian probability distribution of genome size in the population (estimated density on the right axis) is shown by the grey smooth line. The subspecies type strains and strain 23K are indicated by asterisks. (B) Boxplot showing genome size distribution of *L. sakei* isolates according to their genotypic clustering. The horizontal black line is showing the average genome size of 2,020 kb. Clusters E and F showing few variations between them were pooled together for the analysis. For clarity, unclassified strains 332, LTH2070 and 21 were grouped with cluster H.

This analysis revealed important differences in genome size between the *L. sakei* strains. The mean chromosome size is 2,020±30 kb for the species, but the size is ranging from 1,814±30 kb (strain CTC427) to 2,309±79 kb (strain LTH677) representing thus about ~25% of genome variation (~500 kb). More striking is the observation that the chromosome size of *L. sakei* strains was not homogeneously distributed along this range (FIG. 2A) and a Gaussian probability distribution of the genome size data was suggesting a possible division of the strains into sub-populations.

Figure 2B:
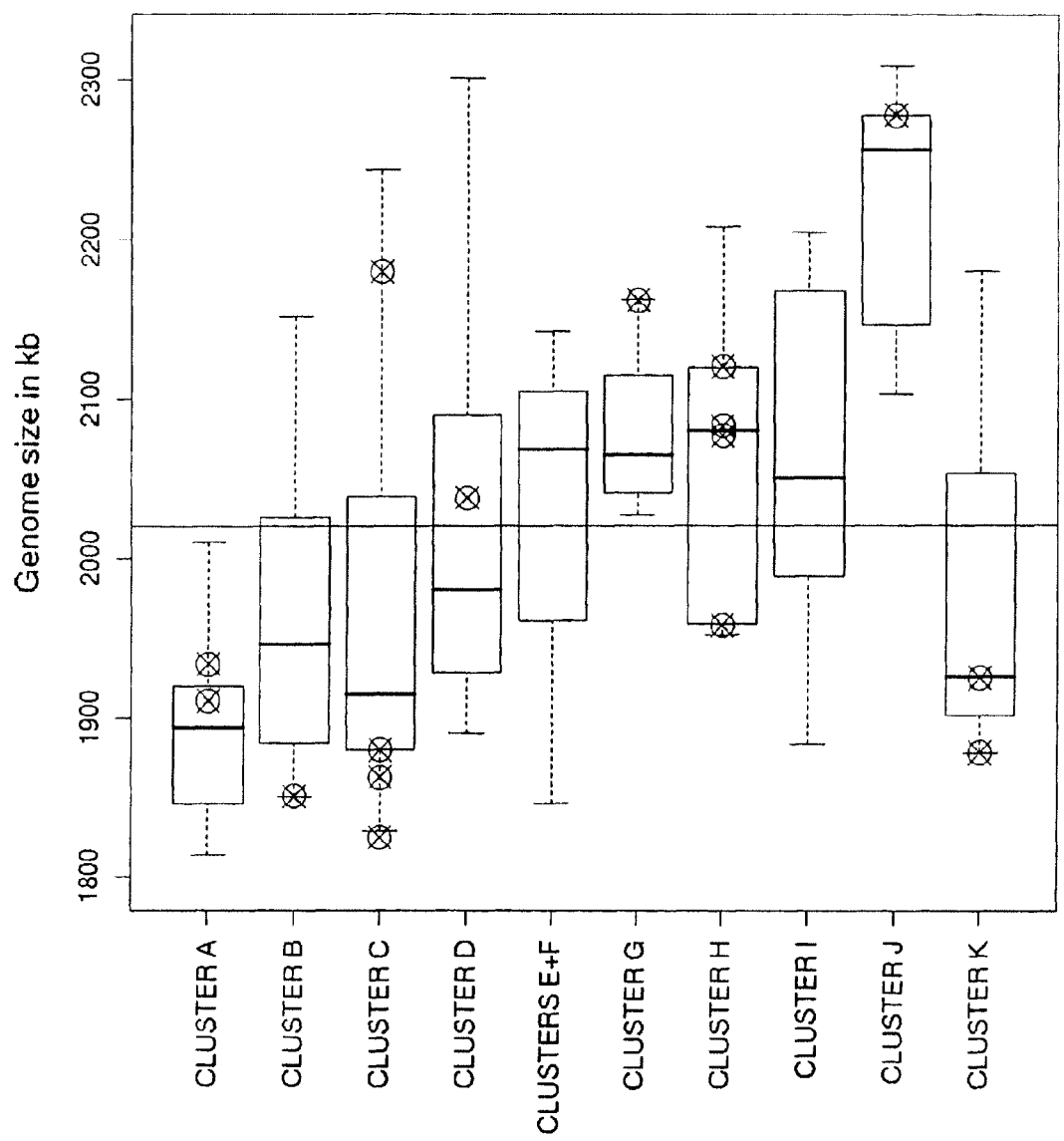

To assess whether the PGFE subpopulations could be explained by the distribution of the strains in the various genotypic clusters, the inventors analysed the genome size distribution across the 11 clusters (FIG. 2B). They demonstrated that the genome size was relatively uniform among strain clusters. They also showed that *L. sakei* isolates from group 1 (clusters A, B, C and D) generally harbour small genome (average size of 1,915 kb±79 kb), whereas groups 2 (clusters E, F and G) and 3 (clusters H, I, J and K) comprise most of isolates with larger genome (average size of 2,055 kb±80 kb and 2,080 kb±80 kb, respectively).

This good agreement found between genotypic clusters and PGFE subpopulations prompted the inventors to analyse the correlation between the genome size of the whole chromosome and that of each of the I-CeuI-digested fragments in the 73 *L. sakei* isolates. A good correlation was observed, as these two parameters were showing proportional increase from the smallest *L. sakei* genome to the largest one.

TABLE 3

Description of genes from the flexible gene pool of *L. sakei* 23K strain used for clustering analysis.

| Genomic Island | Gene name or locus-tag | Product description | GenBank Accession N° |
|---|---|---|---|
| Island 1 | LSA0088 | Adenine deaminase | CR936503 |
| Island 2 | LSA0118 | Hypothetical protein (Putative cell-surface collagen-binding protein) | CR936503 |
| Island 3 | LSA0157 | Putative hydroxyl/aromatic amino acid symporter | CR936503 |
| Island 5 | LSA0165 | Putative oxidoreductase, short chain dehydrogenase/reductase family | CR936503 |
| Island 6 | LSA0172 | CscC-type cell-surface protein with Invasin/Mucin-like domain and WxL domain | CR936503 |
| | LSA0178 | MarR-type Transcriptional regulator | CR936503 |
| Island 7 | LSA0211/0212 | CscC-type cell-surface protein with adhesin-like domain and WxL domain (authentic frameshifted gene) | CR936503 |
| | LSA0216 | MarR-type Transcriptional regulator | CR936503 |
| Island 8 | LSA0217 | Putative transcriptional regulator with a Rhodanese-like domain, ArsR family | CR936503 |
| | LSA0218 | Thioredoxin, TrxA1 | CR936503 |
| | LSA0219_b | Putative cyanate transport protein | CR936503 |
| Independent gene | LSA0306 | L-aspartate-beta-decarboxylase | CR936503 |
| Independent gene | LSA0439 | Hypothetical extracellular lipase/esterase precursor | CR936503 |
| Island 11 | LSA0509 | 2-amino-3-ketobutyrate coenzyme A ligase (Glycine acetyltransferase) | CR936503 |
| | LSA0510/511 | L-threonine dehydrogenase (authentic frameshifted gene) | CR936503 |
| Independent gene | LSA0529 | MarR-type Transcriptional regulator, putative peroxide stress regulator OhrR | CR936503 |
| Island 12 | LSA0564_a to _c | Putative bacteriocin-like peptides (LSA0564_ab) and cognate immunity protein (LSA0564_c) | CR936503 CR936503 |
| | LSA0565 to 0566 | Putative bacteriocin-like peptides | CR936503 |
| | LSA0567 to 0569_b | Putative bacteriocin-like peptides (LSA0569_ab) and cognate immunity proteins (LSA0567 and LSA0568) | CR936503 |
| Independent gene | LSA0572 | Threonine deaminase (Threonine ammonia-lyase) | CR936503 |
| Island 14 | LSA0724 to 0725 | Hypothetical proteins | CR936503 |
| | LSA0727 | Hypothetical cell-surface precursor | CR936503 |
| Island 15 | LSA1006 | Putative zinc-containing alcohol dehydrogenase (oxidoreductase) | CR936503 |
| Island 16 | LSA1182/1183 | Putative Cytochrome P450 (authentic frameshifted gene) | CR936503 |
| Island 17 | LSA1220 | Triphosphoribosyl-dephospho-coenzymeA synthase | CR936503 |
| | LSA1222 | Oxaloacetate decarboxylase, alpha subunit | CR936503 |
| | LSA1227 | Citrate (pro-3S)-lyase ligase (citrate lyase synthetase) | CR936503 |
| | LSA1232 | Citrate: Mg(2+)(H+) symporter | CR936503 |
| Island 18 | LSA1283 | CscC-type cell-surface protein with WxL domain | CR936503 |
| Island 19 | LSA1509 | Hypothetical protein, sigma factor-related | CR936503 |
| | LSA1510_a to _c | Putative teichoic acid/polysaccharide export protein complex | CR936503 |
| | LSA1510_d to _f | Putative Glycosyl transferases complex | CR936503 |
| | LSA1510_g | Putative priming glycosyl transferase | CR936503 |
| | LSA1512/1513 | Putative polysaccharide biosynthesis protein, chain length determination | CR936503 |
| Island 20 | LSA1572 | Putative teichoic acid/polysaccharide glycosyl transferase | CR936503 |
| | LSA1579/1580 | Putative teichoic acid/polysaccharide export protein complex | CR936503 |
| | LSA1581 | Putative teichoic acid-binding N-acetylmuramoyl L-alalanine amidase (cell wall hydrolase) | CR936503 |
| | LSA1584/1585 | Putative teichoic acid/polysaccharide glycosyl transferase | CR936503 |
| Island 21 | LSA1640 | N-acetylneuraminate lyase | CR936503 |
| | LSA1641 | N-acylglucosamine-6-phosphate 2-epimerase (N-acetylmannosamine-6-phosphate 2-epimerase) | CR936503 |
| | LSA1642 | Putative Solute: Na(+) symporter | CR936503 |
| - | LSA1720 | Hypothetical protein (*E. coli* plasmidic gene) | CR936503 |
| Island 22 | LSA1724 | MarR-type Transcriptional regulator | CR936503 |
| | LSA1730 | CscC-type cell-surface protein with bacterial adhesin-like domain and WxL domain | CR936503 |
| | LSA1731 | CscC-type cell-surface protein with Haemagluttinine-like domain and WxL domain | CR936503 |
| Island 24 | LSA1806 | Hypothetical protein associated with CSC-type cluster | CR936503 |
| | LSA1809 | Hypothetical extracellular protein precursor associated with CSC-type cluster | CR936503 |
| Island 27 | LSA1874 | MarR-type Transcriptional regulator | CR936503 |

TABLE 4

Description of genes from other strains than 23K used for clustering analysis.

| Strain | Gene name or locus-tag* | Product description | GenBank Accession N° |
|---|---|---|---|
| Lb674 | sspT | Sakacin P ABC-transporter, ATP-binding and permease protein sspT | Z48542 |
| Lb674 | sspA | Bacteriocin sakacin P precursor (Sakacin 674) | Z48542 |
| 21 | FGP21-0001 | Putative bacteriocin immunity protein | EU391636 |
| KG15 | dsrB | Cell-surface dextransucrase precursor (sucrose 6-glycosyltransferase) | AY697434 |
| 332F | FGP332-0001 | Putative 6-phospho-beta-glucosidase | EU402602 |

TABLE 4-continued

Description of genes from other strains than 23K used for clustering analysis.

| Strain | Gene name or locus-tag* | Product description | GenBank Accession N° |
|---|---|---|---|
| 332F | FGP332-0002 | CscC-type cell-surface protein with bacterial adhesin-like domain and WxL domain | EU402603 |
| 332F | FGP332-0003 | Hypothetical cell-surface protein | EU402604 |
| 332F | FGP332-0005 | Putative pyridine nucleotide-disulfide oxidoreductase | EU402605 |
| 332F | FGP332-0006 | Putative ferritin-like DNA-binding protein (oxidative damage protectant) (dps-type) | EU402605 |
| 332F | lacC | Putative tagatose-6-phosphate kinase | EU402605 |
| 332F | lacG | Putative 6-phospho-beta-galactosidase | EU402605 |

*nomenclature used was as follow: Flexible Gene Pool-strain nam-CDS number

Global Proteomic Variability Between L. sakei Isolates from the Different Clusters.

The inventors then used two-dimensional electrophoresis to compare the proteomes of a selection of 12 strains chosen from the various genotypic clusters A to K as a final verification of the clustering. Although an average of ~400 spots were commonly observed in the Pi range of 4 to 7, they noticed a remarkable variation of more than 20% in this number of spots detected between the strains.

Spots representing major differences were identified by using MALDI-TOF mass spectroscopy. Most of the differences revealed to be strain specific spots of moderately or weakly expressed proteins or to proteins likely encoded by genes not present in L. sakei 23K since they could not be identified in the protein database from this reference genome. Some variations in the 2D-protein pattern were also found to be the consequence of migration differences of some strain-specific isoforms of highly expressed proteins. This information was particularly interesting because analysis of SDS-PAGE protein profiles, the technique used in other studies to define the L. sakei subspecies, is mainly based on the detection of highly expressed proteins. These data further confirmed the hierarchical clustering shown in FIG. 1.

In conclusion, the inventors provided a first insight into the possible number of molecular subtypes within the L. sakei species. From the above results this natural population can be observed as three main groups of strains, each of them subdivided into 3 to 4 clusters. There is a substantial difference in genome size between isolates of group 1 (avg. 1,915 kb) from those of groups 2 and 3 (avg. ~2,075 kb for both).

The inventors evaluated the extent of intra-species genomic variation of L. sakei species and generated, for the first time, a comprehensive classification of the natural isolates.

Example 3

In this example, the inventors have performed a PCR-based detection of 29 genetic markers taken from a pool of variable genes for hierarchical clustering of the strains.

All of the L. sakei and L. curvatus strains used in this study are described in Table 2.

The gene contents of the strains tested were described by using a two-character matrix (genes×isolates) with 0 for absence and 1 for presence of a gene. Similarities between the strains were determined using the Jaccard's correlation coefficient (or Jaccard index) as defined above.

A screening similar to the one described in example 2 was performed by the inventors, and resulted in the selection of only 29 marker genes summarized in Table 1.

Based on the PCR analysis of these only 29 genes, the inventors classified the L. sakei natural isolates by using unsupervised complete-linkage hierarchical clustering algorithm and by estimating P-values via multiscale bootstrap resampling to assess the uncertainty of the clustering analysis. From the resulting dendrogram, 11 bootstrap-supported clusters of strains were clearly identified, designated A to K (FIG. 3). These clusters of strains are very similar to the ones described in Example 2, obtained using about 60 marker genes.

Accordingly, the present inventors were able to identify 29 genes that were sufficient to classify correctly the L. sakei natural isolates.

The invention claimed is:

1. A method for classifying a *Lactobacillus sakei* strain into a subfamily which comprises the steps:
   a) determining the presence or absence of the marker genes LSA1641 (SEQ ID NO:1), LSA1182 (SEQ ID NO:2), LSA1183 c (SEQ ID NO:3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29) in said *Lactobacillus sakei* strain;
   b) analyzing the pattern of presence or absence of said marker genes of said *Lactobacillus sakei* strain and calculating a Jaccard index or Dice coefficient or any binary distance matrix with regard to a set of reference *Lactobacillus sakei* strains; and
   c) classifying said *Lactobacillus sakei* strain into a subfamily according to the analyzed pattern of said marker genes.

2. A method of quantifying a specific *Lactobacillus sakei* strain in a sample containing *Lactobacillus sakei* strains comprising the steps:
   a) genetically characterizing the *Lactobacillus sakei* strains present in said sample by determining the presence or absence of the marker genes LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29) in said *Lactobacillus sakei* strains,
   b) determining the marker gene(s) which is(are) differently present or absent in said specific *Lactobacillus sakei* strain with respect to other *Lactobacillus sakei* strains present in said sample, and
   c) amplifying said gene(s) determined in step b) by quantitative PCR.

3. A combination of markers enabling for characterizing a *Lactobacillus sakei* strain which comprises the marker genes LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29).

4. A DNA array which comprises a combination of markers according to claim 3.

5. A method of comparing at least two *Lactobacillus sakei* strains comprising the steps:
   a) determining the presence or absence of the marker genes LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29), in a first *Lactobacillus sakei* strain, and b) determining the presence or absence of said marker genes in a second *Lactobacillus sakei* strain, wherein, if the pattern of presence or absence of said marker genes is different between said first and said second *Lactobacillus sakei* strains, then the *Lactobacillus sakei* strains are different.

6. The method according to claim 5, which further comprises the step of analysing the pattern of presence or absence of said marker genes by calculating a Jaccard index or Dice coefficient or any binary distance matrix.

7. The method of claim 5 wherein said steps of determining the presence of absence of marker genes are performed employing a DNA array which comprises a combination of markers enabling for characterizing a *Lactobacillus sakei* strain which combination comprises the marker genes LSA1641 (SEQ ID NO:1), LSA1182 (SEQ ID NO:2), LSA1183_c (SEQ ID NO: 3), LSA0172 (SEQ ID NO:4), LSA1731 (SEQ ID NO:5), LSA0211 (SEQ ID NO:6), LSA0212 (SEQ ID NO:7), LSA1579 (SEQ ID NO:8), LSA1580 (SEQ ID NO:9), LSA0118 (SEQ ID NO:10), LSA0529 (SEQ ID NO:11), LSA0439 (SEQ ID NO:12), LSA0572 (SEQ ID NO:13), LSA0219b (SEQ ID NO:14), LSA0564_a (SEQ ID NO:15), LSA0564_b (SEQ ID NO:16), LSA0564_c (SEQ ID NO:17), FGP21-0001 (SEQ ID NO:18), sspA (SEQ ID NO:19), spiA (SEQ ID NO:20), FGP332-0001 (SEQ ID NO:21), FGP332-0002 (SEQ ID NO:22), FGP332-0007 (SEQ ID NO:23), FGP332-0008 (SEQ ID NO:24), FGP332-0009 (SEQ ID NO:25), FGP332-0010 (SEQ ID NO:26), FGP332-0011 (SEQ ID NO:27), FGP332-0012 (SEQ ID NO:28), and FGP332-0013 (SEQ ID NO:29).

8. The method according to claim 1, wherein the presence or absence of said marker genes is determined by amplification.

9. The method according to claim 1, wherein the presence or absence of said marker genes is determined by hybridization with probes specific for said marker genes.

10. The method according to claim 2, wherein the presence or absence of said marker genes is determined by amplification.

11. The method according to claim 2, wherein the presence or absence of said marker genes is determined by hybridization with probes specific of said marker genes.

12. The method according to claim 2 wherein a classification of said *Lactobacillus sakei* strain is performed by analyzing the pattern of presence or absence of said marker genes and calculating a Jaccard index or Dice Coefficient or any binary distance matrix with regard to a set of reference *Lactobacillus sakei* strains.

13. The method according to claim 5, wherein the presence or absence of said marker genes is determined by amplification.

14. The method according to claim 13 which further comprises the step of analysing the pattern of presence or absence of said marker genes by calculating a Jaccard index or Dice coefficient or any binary distance matrix.

15. The method according to claim 5, wherein the presence or absence of said marker genes is determined by hybridization with probes specific for said marker genes.

16. The method according to claim 15 which further comprises the step of analysing the pattern of presence or absence of said marker genes by calculating a Jaccard index or Dice coefficient or any binary distance matrix.

* * * * *

SEQUENCE LISTING

```
<160> NUMBER OF SEQ ID NOS: 29

<210> SEQ ID NO 1
<211> LENGTH: 696
<212> TYPE: DNA
<213> ORGANISM: Lactobacillus sakei
<220> FEATURE:
<221> NAME/KEY: misc_feature
<222> LOCATION: (1)..(696)
<223> OTHER INFORMATION: LSA1641

<400> SEQUENCE: 1
ttgaaaaata attttttgga taaggttaaa gatcgattaa tcatatcatg tcaggcatta      60
gcggatgaac cattacacag ctcatttatc atggcacgaa tggcacgagc ggcttatgaa     120
gcaggcgcta gtgcaatcag ggctaattcc gtagtagatg ttcaggcaat tatggatacg     180
```

```
gttgagctac cggtaattgg gttggataaa gtagattatt ctgatgcacc catttatatc    240
acgcctacaa tcaaagaaat gcgtggcatt gctgccactg gtgcagcagt tgttgcttgc    300
gatgttacgg ggcgtccacg acctcacggt gaacaattag caacgattgt cgaaacaatg    360
cggactgagt atcctgatac attattaatg gccgatacgg ccagtcttga tgatgtgaaa    420
gaagccaacc gattaggttt cgacattatt ggtacgacaa tgtatggtta tacaccggct    480
acggaaggct gcaatattgc cgataatgat tttgaatatt taaaacaggt tttagcgatg    540
tccaaggcgc ccgtaattgc agagggaaaa atcgattcac ctgaaaaagc agtcactgct    600
ctaaaattag gttgtcatag tgtcgttgtg ggatcaagta tcacacggcc acaattgatt    660
gctaaaactt atattgatgc cgttaatgaa ctataa                              696
```

```
<210> SEQ ID NO 2
<211> LENGTH: 627
<212> TYPE: DNA
<213> ORGANISM: Lactobacillus sakei
<220> FEATURE:
<221> NAME/KEY: misc_feature
<222> LOCATION: (1)..(627)
<223> OTHER INFORMATION: LSA1182

<400> SEQUENCE: 2
atgtattata tcgaacagtt tgtccgtaat tccatcatag gagccgagtt attaccagta     60
gaggttgcag cagttgaatt gctaaacatc attcgtccta ctgtagcact gacggtttgg    120
atggccttaa tggggcatgc gcttttcagt aaaacgaact tgtatgacca attaaaagaa    180
gactttgata ccctacaaga ttcctttatt caagaaatgc gtcgctacta tccattcttt    240
cctatgttac cagcaatcgc tcttcgtgat gtagaaattg atggttacga ataccaaaa    300 gatagctggg ttgtcttaga tatttatggt acaaaccatg acgctcgtac gattgatcat    360
ccagaaaaat tgatatcaa gagatatatt ggaaaaacaa agaaatttc ttatgaagaa      420 gaatacgaaa tgattgcgca aggtggagga gaatttagaa atatgcaccg ttgtgcagga    480
gaatggatta ctcttcacag tatgcgtgtc ttttctgacc aattagtaaa taaatataac    540
tttagtattc ccgaacaaga ctggaccgtt ccaatgaacc aatttcctac gtatccaaat    600
agtaaagcat tgttgtttaa agaataa                                        627
```

```
<210> SEQ ID NO 3
<211> LENGTH: 753
<212> TYPE: DNA
<213> ORGANISM: Lactobacillus sakei

<400> SEQUENCE: 3
atgaaacaag taccagaaac aaaaatcaaa ctaacggatg taaaggagtt gattaataaa     60
gggtataacc ttttaggtga gcttcgtgaa gaagcagatg ctccagtagc aaaagcagaa    120
tttctgacag aagaaattac aaccgtttat ggagaagaag cagcgcgtaa attttataat    180
cctgaaaact tcaagcggga agggtctatg ccaaaagtag tattgaaaac tttatttggt    240
gaagacggcg tacagacgat agatggaaag aaacaccatc aacgtaaaaa ttatttcatg    300
gatttgatga ctccagaacg tatgaagac tatagagcta ttctagatca aaatcttgca    360
accgaactcg atcagcaaca tggcactttt gagttattcg acctttctaa aagagttctc    420
tttaactcta tttgtgaatg ggctggaatt aatctagcac agtatgatcc gaaagaaatc    480
gataagcttg ctagtaatca aatatccatg attagcggag ccatcacttc tccaacgaac    540
cacttaaaag gagtaaaaga ccgtaacgaa tcagagggat gggctcaatc attaattaaa    600
```

```
gaagctcgca aaaatcctgt accaggcaaa gaaaatcttg ccctctatac attcgcacaa    660
gcagaagacc tagaaggaga gggctcctat gtcaagaatc cggacataaa agtacgaaca    720
aatttgactt tcaatttaaa ttacttaatt taa                                 753
```

<210> SEQ ID NO 4
<211> LENGTH: 3912
<212> TYPE: DNA
<213> ORGANISM: Lactobacillus sakei
<220> FEATURE:
<221> NAME/KEY: misc_feature
<222> LOCATION: (1)..(3912)
<223> OTHER INFORMATION: LSA0172

<400> SEQUENCE: 4

```
atgttcagtt tggcgttact agcagtaatg ggtatacaac tagttgttac taccggaacg     60
atccttgctg aaaatagtat caaagtagat tcaaatcttg cgttaacatc ggatcaggaa    120
ttatctaatg aaaaacaaat tgtaattaga gcgagcgatc agtcaaaagc gcaacgtgat    180
ttagcgctaa ctataccaga gggggccaca tttgatcgca aactagtaa tcaattaaac     240 aaaaaatcag cgtatacggc taccttgat caaaaaaata attccaatca agttatttta    300
aaacaaacag cacaaacagc tgaaaatatt gagaatgatt tggtaaatag caagcaaca    360 acgttcaaaa aagaatactt attagttttt aaactaaaag atactggtat atccgctaaa    420
caacagttga aagtgacaac aataatgaac gggattcgct atgaatctaa accactattg    480
ctgaaagagg tcgttggaac agatggtgtt caacgacaaa ctagtttgac gaaggagggt    540
gaacctcaaa taacctttaa tctaaaccaa acagaatata tcgttggaga taccatccag    600
ttaaaagttg atcttgatgc tagcgaaatt aatgaacctt tctatattaa tcttggcaat    660
aaagcaatac taacgccgat aaaagtatct agcgataaca ggaatattaa ctttgaatca    720
caaaataatc agaatacagg gaagaacatt ttaaagattt ccagtaacga accgataaag    780
aaagatttta cgctactagt aaaagcgaca acagttggga aggtcgatat tactgcttct    840
accgaaactg atcatttaat ttcgaagaca gctactgtta agtggttga taacccaaca    900 tcaaaagtat tagcaattaa tcccaatact tttgatgacg gtattcctaa ttgggttcaa    960
aagacaaaaa cagaggtcgg aagtaagtct tttcaaagaa gtacaagtcg atttcttaat   1020
tataccttcg gtggtgtgaa tggtggaatt gatgcagaag cagattcaaa aatttctagc   1080
tacaatattc agggtagcca gattaatatc tttattaaag ataacaataa acaatcggc    1140 gctttttta agggagaaga cactagtagt aaagcagtaa gaacatcaac cggttttggg   1200
attgttttcg aaccaaatga aagtaatgat ggacctaaac aagctatctt agctaacaag   1260
ttaacaaata aggcatattg tgtcggacac gacagcgagg gtaaccttgt tagcaaaata   1320 ataggcagt ttgaacgtaa tgggaagaca ttaattgctg aaattctatt gcggccttca    1380
ctatcaggta ctactgcggt tcaacaagag ctttatttga aaaatgacac aactcaatcc   1440
gtttcttatg ggacctttat tggtcaagat acaatgttaa acggtaatga taaagtaccg   1500
atgtcatcaa tgggcaataa cgcaggatta tatatcactc aaaatcccta taaattggcc   1560
atcaatatga aggttcctga tggaccaatt aattatgcgg cacaaacttg gactaggaga   1620
aatccttggt ttgatgggtt cacaccacgt aatttttctg gaacgggctt ggaacaaaag   1680
aatttagaag agggttacac agttttaaaa aattccgata cttcatatac agccaagtgg   1740
ccgtttgcta ccttggcccc tggtgaatca aacattatc gtcaagatat agggattact   1800
aaagcccctg acgttgcacc agaagcttat aaagaatatc aaaatgaaac tagtactgat   1860
```

```
gggagtaata gaccaggcga taatataaag tttacattac gtgctcataa ttcgggattg   1920
gattcttctt ggagtgatgt ttcgtttagt gatattattc cgtccgaatt tcaaattaat   1980
acaaattcaa taaggttaat aaataaaagc ggtcaagaaa taaccatttc accgtcagct   2040
tacaatgaag taactcgaga gttgaaagtt acggttccta acagtgttaa agataaccag   2100
tgggttagtg tcacatttga agcgaaggct ttaactacag cttctgggcg aactgttcgt   2160
aacactgtca atgttgttgg tatagacagt aatgttaatc aacaagaacg ttcagcaagt   2220
gcgatagtcg atgtaccgtt tatcaaagta caattccag aattaacgaa aaagtaaaa    2280 aatatttcta gattagatgc gaagtatgct actgaaacag aagcaagtat tggcgatgaa   2340
attggttata aattagtttt cactaacact aattctgagg aagtaccgga ggccattatt   2400
gaagatccgc tcgattctga tctagatgaa ccaagcgctg ttcatgttag ttataaagat   2460
tcaaacggga gtgaggtgag aagcgaagac ttaaccttta ctggtaatca attaattta   2520 aaagctatcc cagcggatgg aagtgtggtg ctaacttttg agactattct caaagacact   2580
aaaaagaccg ttattaataa tatagctatg gttgctgatg ttaaatcaaa tgtcgctaaa   2640
gtcaatgtta tcaaaaaaac accaccaacc ctaattaagg aagttaaaaa tataacgaag   2700
tccgacgcag attatatgac agaaacaacg gctgaagttg acgatgagat tgaatatcgg   2760
atacaaattg ttaacactgc ctcaggcgat attaaaccgg gtgcaatatt aaaggatgtt   2820
tttgatgctg acttaggtga tattcaacaa gttagaattg attatttgga caaagatgaa   2880
aaaattattg cgaagcaaac aactgattgg actgataacc aggttatctt ggatcatggt   2940
attccgattg cgggtcaagg tatggcgatt gcttatgtca aagccaaagt aaaagagact   3000
aataaatcag tgattaataa tagtgttagt ctggacaccg attttggagc tggggcttct   3060
gaaaaagcca aattaaatat taaacagtct aaaggccgga ttgttgttcg ctatcgggac   3120
cgaaaagatg aaagccacaa gttggccgaa gatgagacct ttgatggcaa aattgggaac   3180
actagactag tgcaacccaa agttattcca gaaacagacg gcaattggac cgtggttgat   3240
tcttctaata tggtagatcc agattggggc tcaaccacga aacctgattg gacattggct   3300
catgatcata ctgtcactta cgccaaagat gaacaagtca ttacttatcg atatgaagaa   3360
tcccacattg gcattattgc cgataaacgc tgggattttg gtaaacatga tacgactggc   3420
actgaccgaa actattatct aaaagctaaa actaaagaca atcaaaaaca gccatacgcc   3480
gtcagcgttg aggattacta cacctctaag ggttggactt taaatgttaa acaagatgat   3540
cagttccata ccaatgctaa tgaaaagatt gctggagatc aaaaattctt agataatgcc   3600
gtcttaaatt tccataatgg gcagattgtc ttaaaagaaa gtgatgacgt agggggcaacc   3660 gccccagttt ctaaggtaac ttctgagttt gagttaacac caaaggcgc ggcagttaat   3720 ttaatgacgc acaccaataa gacacctaat cctggttatt atgccgcaca tggctttggg   3780
atttgggctt atcaatttgg ggatgcccaa caggctgatt acagcattgg tttgaaagtg   3840
cctaaagcaa caaaacgatt cccaagacaa tatacaagcc aattaacttg gtcattagta   3900
atcgcagaat aa                                                       3912
```

<210> SEQ ID NO 5
<211> LENGTH: 5307
<212> TYPE: DNA
<213> ORGANISM: Lactobacillus sakei
<220> FEATURE:
<221> NAME/KEY: misc_feature
<222> LOCATION: (1)..(5307)
<223> OTHER INFORMATION: LSA1731

<400> SEQUENCE: 5

```
atgaagaagc gaataatcta tagtttatta ataattttgt tattaatgac aactgttttg      60
cagtcactag gtactgtatt tgcggcagca actgccaata atagtagtga aacaacatct     120
aaaataatag atactagtaa atcgattgca caagtgagtg agtcttcgca acttcgaagt     180
agcagccaga atgttgtgca atcttcgagt acaagtcaga aaaagaaag taagaagagc      240
tctagttcga attcaacagg taagtcggtc atgcaaagtg catcattgtc ggcggctgat     300
gatactggac taacattcca tcaaggtaag ttagcacttg gtggtgggaa ctacttagcc     360
tatacaaatg ggacgaacta tgatgggatt cgaggtaaga caccgactat cactgatcag     420
tcgatttcct atgctaattt tgtagcgggt aaagttcaag gggtaccaat tactaagacc     480
ttgatggaac acgctggacg gaataatatt ggtttatggg cacaaggtgc gaaagatttt     540
ggacaataca cacgttggat gtcaattcat aaagatgatg taaataaatt tgatattgat     600
cttggtgcag atacaccgat tgcccccaat caagctgatt tgagttttac aaatttaagc     660
tcctcgacaa ctttactttt tggcttagag gctgataatg cgattggaac aagtggaaca     720
ataaaagtta cggcatcatc attagaagca caaggaacta ttttgaagca gactttagaa     780
tatacacgta cggtcggtgg tgctgcgact acaattactg atgatgtaac gtaccaacca     840
actgattgga gaccgtctca cattaaggag cacatccacca atacttctgg tcgtgattta     900
aaaggcctct tctttggtcg aacaattgat actgatttac ggaattttgt gactagtgac     960
caagggtcag gtgccattgg agataagcca aaacttattg ctgatggtga tcgcggtatg    1020
tacgagaaac aagatatttc agcaacagaa ggtccaacta agtatcagga agggaatgct    1080
tctttatttt atgattttaa tcttttcaat ggttctggtc ctgatggttg gcaaggcttt    1140
aatctcacaa atgcgcccac aagtatccca tcaactttta ttggtaaacg atttgcgaca    1200
ccacgtgcaa aaggagatcg aacgacgaag gtaaacatcg ataccgaact cgacatgctc    1260
tggtggccta aagatttaaa acaaggtgaa tcgcgggata ttggctatga agttggttta    1320
aatggtgggg gtcaaccaag tccaccggaa atcactttga atcaaaagcc gcgagtaatg    1380
tatgttgatg gtagtcaaaa ggatgttgtc ttagacggga cagtgacgaa caaaaaccca    1440
actgattcag ctgatcctaa atacaagaag atgaatgaat taatctatta tgaagtgcaa    1500
cataaagatg ctagtggcaa tgtcacgacc ggtggcccta agttctgac atcagtcgca     1560
gatgttgcgg ctggacaaac caagaattat tctggtctag ctaaagggat tgaagatgac    1620
ctacacgtcg gtgatcggat tgttgtctgg gctgtcgata gtggagggat gacttccgtt    1680
aaccatgaac acactgactt agtagaacgt gcggctgaga ttagcaaaaa ggttaagaat    1740
atcacgaatg gagattcaag tttcaagacc gaaaccgact ataaaccggg tgatacggtt    1800
gaataccaag ggacgttgaa gaatcttaaa acgaaagtag ccttacctaa gggtgcaatt    1860
attactgatg aattagactc aaacttgacc gtcaaaggtg atgtaacgtt aacttactat    1920
gatgcgaatg acacgcagat tggcgcagct caaaccactt cgtttgatag taatacgcat    1980
actgtaaaaa ctgctaatga aattccagtc ggcggttacg tcgtgattga cttcaaggct    2040
aatgttgcta agaccgcaac aggtgatatt gataatatca tgcggtctaa ggttactgtt    2100
actgaaaaag atacacaagg taatgaccaa acatatgaag ttaatacaga tccatcgaat    2160
aaagcgataa tccatccagg tgaagaccgt gaagttcaag attttaaaaca gtacattaaa    2220
cttgatacca cactgattg gacattaggg acaaccgggg ttactgggca tcgtaaggat    2280
aaagttaact acaaatttgc atttactgct aaaaagagca attcggctgg aattagcgat    2340
```

```
gctgaaatca gcgacattaa gatggcgcct gatgaattaa cagcaccaac gaatgtaaaa      2400
gttaagatta taacgccttc tacgactaaa gccgatacat cagaaacagt tgatgggaca      2460
gctacaccaa gtagtgatgg tgagacttat tccattaaga ttgataagtc aatcaaagct      2520
ggtcaaaagg ttgaagtaac attcgatcga acagttaatg atgatgcaac aatcgatacg      2580
acaacaacag aacatgatca aacagggaag ttaacagcag cttcgttaag tacaccgatt      2640
gccgataagg ataactttaa ccttgcaaaa ttaaagattg aagaccaacc aataacggta      2700
actgatctaa aacaaacgat tagtaataca accacaccag caaatgataa gaatgatgca      2760
acaacgcatg ttgctgttga acgtcaggt aaacaaaatg acatcattca atatacgttt       2820
actggtaaag ctggggataa cacagacgct ataaaggatc ttctgctttc ttcttttaac      2880
atgaataaac caaacgaaat gtcttatatt gatgattcat tggaaattac gattggctca     2940
gaggtacagg aaaaaacacc gcaggttcca ggtaatggta acaccgttaa gattacaagc     3000
gacttgccta agaatcgac ttttaaagta acctatcaga tgaaggttgt aaatgatgtc       3060
gcgaatacaa ttccaacga tgcaaagtta tctgccacaa acttaaaagc aacaccattt      3120
aatacaacga ccttgaatac agccgcggct tcaaatacgg cgacaatcaa gcaattcatt     3180
aagaaccgga atacggctgg tgaaacttgg aaaggtccta atgtgactgg tgataaagct      3240
gaaacaagtg gtgttccagg aaacattatc gattacaaat ttgctattgc accaggtgcg     3300
aagaatagcg ctgatttact agatactgct ttgaaagata ttgcgatgaa agaatcgagt      3360
gggatgactt tagttaaccc agaaggttct atggataata caaagcaggt gaaagtcaca      3420
gttgatggtg tgacaccaca atatattagt ggtaatccca tcagtgcgaa tgcagaatta      3480
aacgatgtct tcacgccatt aacaaaaggc aaagggatga caattgagta cagcgctaag      3540
atcaatgata acgctggtac gcaaaatgtg acgaacgatg ctaacttcta cgcatcaaac      3600
ttaacgggtg atatgccagc aacctcaaca gtagctgaca aggcacataa aacaccagct      3660
aacaaatcaa ttttacacat tgtgcgtaaa gataacgtca caatcaaaca agaattgaaa      3720
caagattcgg caaccacctt taagacgacc gaaactggtg ttaaaggcga tacaatcgac      3780
tatcgtttca tggttactgc tggcgatgat aatagtaccg atattaagaa tattgtcatc      3840
gataacattg tgatggatcc agccggcaag ttggattacc aagctggcgt cacagcaacg      3900
cttcagggga cagcgctccc tgctggggat gtcgtcatga gtgatggcac aacagccggc      3960
acgaagaaga ttacggttaa gaatgtttca ttgtcgaaaa cacaattatt aattgtgaac      4020
tacaagatga agattacagc ggatatggat ggcgacgtaa caacgatgg gctgttaaca       4080 gctgatagtt tcacggatca gaccaacacc gttgccgctg ataaagggaa atttaataca      4140
actgttttaa ccccttaaaaa gatatccaat aaggcaaaga ttagccaaag tattaatctt     4200
aaagataatg tagcgaatac aaattcagga tggattgggc cggatgaacc ggcgcctaat      4260
aataaacctg cggaagcaac tgttaaccct ggggatacag ttacgtacaa gttttcgatt      4320
aaatttccaa cgaccgatcc gaagaataac gctgatctat tgaatagtgc gttacaagat     4380
attgcgatga atgtaccgga tgatttagag ctagcgaatt ttgtaggtac gactcataag     4440
attcaaatta gctatcggac gggtactgaa ggtcaagttt ctgagtataa cgatactatt      4500
aattcgatta aggacattaa aaaccttgac cttaagagtc cactttctaa gaatgtgaca     4560
gaggctcttg tttactacgg cgctaacatc atgccggatg ctaaaacaca agacgttacc      4620
aacgctgcga acttctacgc atcaaactta acgggtgatt taaagataac gactgttgct     4680
aattatcaaa acaagacaaa agcgaaccaa tcaatttac acattgtccg taagataag      4740
```

```
gtgacaatca gtcaacaatt gaaacaagat aaagcagcag aaacagcttt tggtccaaaa    4800
gcatctggta ctaaaggcga cacaattgat tatcgtttca aggttactgc tgataaagac    4860
aacaatgctg atgttaagga tatcgtcatc gataacattg tgatggatcc agccggcaag    4920
ttggactacc taacaggcat taccgcaaca gcgggtggaa cagccgtccc tactgctaat    4980
gtcactatga gtgatggcac aacgcgggc acgaagaaga ttacgcttaa gaatgtcgcg    5040
ttgaagaaat cacaagtatt aatggtgaac tacagatgaa aggttacagc ggatatggat    5100
ggcgacgtaa acaacgatgg ctttttgaca gctaacgggt ttacagatca gaccaacacc    5160
gctgccgctg ataaaggcaa gtttaataca accacattga cattgaagaa acaaaagaac    5220
acggcaacca ttcaacaatt tattagaaat ccagcaacgg ctatttcggg acaagcgtgg    5280
tttggtcctg gatatggggg atggtaa                                       5307

<210> SEQ ID NO 6
<211> LENGTH: 465
<212> TYPE: DNA
<213> ORGANISM: Lactobacillus sakei
<220> FEATURE:
<221> NAME/KEY: misc_feature
<222> LOCATION: (1)..(465)
<223> OTHER INFORMATION: LSA0211

<400> SEQUENCE: 6
atgacgactg aagtaaatgc tgttgaagcg cctgctaatg cgtcttcgga aacgatcact     60
aaaatagctc aggacgctat ttcaggttca acaccaacta aacaatcaaa tagtgtcatt    120
caaaaaaagg cggcttcaga tgcggaaaca caaaccataa cgccagcaac gtcaggtgaa    180
aaagcgacgc tacttgaagc accgcagact aaaaaaactag ccaaccccaa aagcagtaac    240
ttgatcaacg agcaggcacc agtttgggca cagtcacctg gtatatcgat gatacaacgg    300
cgaccttaca tttatcaggc ggtgtattgc cggataaagt ggctaatgat actactaata    360 cacctggta tttccctaac tcgccttata ttgcgcgaat cgcgcatatc agcattgatg    420
gtgaaattac agctaaagat gtctcctata tgttttgggg gttga                    465

<210> SEQ ID NO 7
<211> LENGTH: 3135
<212> TYPE: DNA
<213> ORGANISM: Lactobacillus sakei
<220> FEATURE:
<221> NAME/KEY: misc_feature
<222> LOCATION: (1)..(3135)
<223> OTHER INFORMATION: LSA0212

<400> SEQUENCE: 7
ttgggcacag tcacctggta tatcgatgat acaacggcga ccttacattt atcaggcggt     60
gtattgccgg ataaagtggc taatgatact actaatacac cttggtattt ccctaactcg    120
ccttatattg cgcgaatcgc gcatatcagc attgatggtg aaattacagc taaagatgtc    180
tcctatatgt tttgggggtt gaccaactta acaacggttc aggggttagc taatctaaaa    240
ggggccacta attttacgat gttatttgcc agtgacagtg cgctgcaatc agttgacgcg    300
actaacttag attttcaaa agtgacagca atgaattcga tgtttagtga ttgtgccaac    360
ctagtatctg ttggcgacac agcgaattgg cagcttgggc aagtcaccac aatggtaaga    420
tgcttcagtg gtgataaaaa attaagtcag ttaaatagta cgaattggga cacttctaat    480
attcaaaata tgaataatac attttttcaat tgtacggcct taacgaactt agatgtttca    540
aaatggcaga cggcaaaaat gactaatctg gggagtacct tttcacaatc gggcattact    600
```

```
gttttagatg tttcaaattg ggataccagt cacgttacta atttaagtag tacttttctg    660
aatactagta ttgccgaatt agatgtttcg aattgggata caagccaagt gacgacaatg    720
gcttatactt tttcgggatg ttcaagactt gaaaccttag atgtctcaaa atggcagctc    780
ggcaaaaata catcgttgtc ttacacgttc agcggtgatc aaagattaac gcagttagac    840
gtttctaagt ggcaaaccgc taatgtgacg aatatggctt caacattttc cgggactgtc    900
ggtgttaaga ctttagcggt taaagattgg cagaccacta aagtgataac catggcgggc    960
atgtttgcca agagtggcgt tgatcagtta gaaattgctg attgggatac gagcaacgtc   1020
caaagtatgc gactcatgtt tgatgcgacg aagttaacaa cgcttgatta tcctgattgg   1080
aataccgcta gtgtaaccga tatgagttat atgctgcgtg ggatgacgaa attaacggat   1140
gcttatttca cgaattggga tacgagtcag gtaacgaata tgggcggcat gttttttgaat  1200
```

```
gggcagtggg cttatcgctt tggtgacgaa aaaagtgccg attatagtat tggttttaaat    3060 gtaccggcaa ctactaaacg atataccggt cattatcgaa cgaaattgac gtggtcacta    3120
tcagttggcc catag                                                      3135
```

<210> SEQ ID NO 8
<211> LENGTH: 1542
<212> TYPE: DNA
<213> ORGANISM: Lactobacillus sakei
<220> FEATURE:
<221> NAME/KEY: misc_feature
<222> LOCATION: (1)..(1542)
<223> OTHER INFORMATION: LSA1579

<400> SEQUENCE: 8

```
atgacagttc gtaacaatga ggcaataaaa aaatatggtt cttttttct ggttttatt       60 ttctttggtt atctatcaat taactttccg ttgactggag atgatttaaa ctgggggata    120
acgactttaa aaaattattt tggatcaggt cagttcttaa attatgatgg acgttacgct    180
ggtaatagtt taattatcat tgctagtcat agtgcggtat ttaaggtttt aagttacgca    240
ggtattacaa cactagttgt ctatctggct gcccatttga ttaacaacgt taggcaatta    300
gaaagaaata cgttattaat tcttattttg atgttaacga tgagtacaga gttgtttgcg    360
caagttttag ggtggaatgc cggcttcttt aactatatgg cttcattggt atatccctta    420
attattatta acttagtgaa gtatcactat tctgattggc aagcatcaaa gtatttacgt    480
tatagtattt taatagcggt tctttcaata atcagttgct tttttgttga acacgttaca    540
ctattaaatt tagcagttgc cacaattttt atgggctata tgctataccaa aaaaaagaaa    600 aactacttag taattgctaa tttcattggc acatatattg gtggcatttt aatgtttttcc    660 aataaagctt atttaaatat attattacat catgacagtt accgggaaac aagttttttca    720 ttgactaagg tttatcatat tatttcacaa caaatggatt tttatctctt gattgataat    780
ccaattatta cagtgttact tgctgtcatt ctgggttact taattattaa aaatctccaa    840
aagcgttcgg gtaataagtt ggggactgtg gtttcttatc tagaattgag tatcctgatt    900
gctttcatag aatatcatta tttttgttt aatacctttt taaaggactt cggccatcgc    960
tatttagtat catgtttatt atcaatttta ttcttattag taattgtaat tgaaatggct   1020
aagttatcac tggaaaccca caatatcgaa tatattgcat taattgcagc tgctattgtt   1080
ttaattgtgc cattctttgt agttacaccg tttggtcctc gaggagcgtt tgcaagttat   1140
ttctgtttgt gtttgctagt agttgcctta tgcaacgaat tgaatgctgt taaatttagc   1200
ttaccaatta tcagaataat gatggtaatg gttgttatct tttatgcggg cttagcaaca   1260
cgaattggtc atgcgagtcg tatcaaaaat gattttataa cctatcagga aaaacataac   1320
acgcctaaag attatcgttt atatctagag gtaccgtata atcaatatta ttgggcggtt   1380
catccacagg ctactgatag tagttacaga gggtattata agattaaaac cataggggc   1440 aagttggtcc catatgctaa atggcgttta attgaaaaga atacgaatag taacgcagaa   1500
atgttttctc aagttttaaa agttgatagt caaaataaat ag                      1542
```

<210> SEQ ID NO 9
<211> LENGTH: 1452
<212> TYPE: DNA
<213> ORGANISM: Lactobacillus sakei
<220> FEATURE:
<221> NAME/KEY: misc_feature
<222> LOCATION: (1)..(1452)
<223> OTHER INFORMATION: LSA1580

<400> SEQUENCE: 9

```
gtgcaaaaat ttatgaacgg ctttgtaaag ggtgtttata cagtactttt ggtaagcatt        60
tttgctttta ttacgtatta ctcaatcagt aatttagtca ccggtaatta cctatctaat       120
tctaaattaa tgattgttgc tattgtcttt tacatattaa ttatcttggc attggtttta       180
ttgaccaaga taaccagtaa aaaaatattc tttatgattg taacgggaat ggcgatatta       240
gtcagaattg gttggttgat taaggtcccg acagcaccga gttctgattt tcaaatgatg       300
catcatgccg cgatactagc gacgcaaggt gacctctcat ttctaaagga aagttacttt       360
caaagttggc cttatcagtt aggctttgtt tattttcaag cattgattat caaaatattt       420
ggtcaaaatg tgcttattct acagataatt aacatccttc taaattgcgg aattgcattt       480
gttgggtata agattattaa tctacacttt aaagaaataa cagggcgcat tgtgtatacg       540
ttattgctat tttatccagc gtatatttat atgacaggtg ttttaacgaa tcaatttcta       600
gcaactttt taatttattt agcaatctat ctatacttaa agcatgatca attatgggtt       660
aaagcaactg ctggtgtttt attagcactc gggaatatga tgcgaccatt gggcattttg       720
ttgattattg cacttgtctg ttttgaaatt acaaaatggt tattggcacc ggatcggaaa       780
aatattttaa aatcactcgg aagagttacc actagtgttt tggcctattt tctcatgttg       840
ttcttagtga atagcgcttt gcaagtaacg catttatccg aatatccgct ggaaaataga       900
aatccaactt ggaaatttgt attagggttg aatgatgaaa ccgttgggag ctactctgca       960
acggacttaa gcttaatgga tcggtatcca cttggcgcaa aacgagataa gctgggcaaa      1020
gagattatta aggaaagaat ccaagataaa cctaagctcg ttaatttaat gttcaataaa      1080
agtaagaaga tgtggactgc tcgggatgat gccctaatgt gggggatggc agataatgtt      1140
aagttatctt taaagattaa aaattggttg aatgcggttc agttttttgtt ctatattttt      1200
attgtagcaa atgccttatt agcagtattc aaatggcgtg aaacatggac ggacggttat      1260
ttattaaaat tgatgatcat cggttatttt atggtccatt tattaattga gattcagtct      1320
agatatcgat ttttcattgt cccggcattt atcatgttaa ctgccatagg ttgggtcact      1380
gtctatgaaa agatccactc aaggcaagca aatgataaaa agactttaaa agaggatata      1440
gtaataaggt ag                                                         1452
```

<210> SEQ ID NO 10
<211> LENGTH: 2202
<212> TYPE: DNA
<213> ORGANISM: Lactobacillus sakei
<220> FEATURE:
<221> NAME/KEY: misc_feature
<222> LOCATION: (1)..(2202)
<223> OTHER INFORMATION: LSA0118

<400> SEQUENCE: 10

```
ttgaatgcgt ctaatgcgca aggaaaagcg ctggctggcg ttcaactaaa gctcaaactg        60
atgggttcta agaaaagtta tgagcgaaca gttacgacaa cggcaacagg taaagctact       120
ttggcagctg tcccagtagg cgactatcaa gtgacgcaag aatcaacggt gatgggttat       180
cagccagcca ctgctgttca gtcattaaca attagtaacg accatcagaa taccgtagat       240
tggcaattgc aacgaatggt agcggatgtt acttttagag ttcgcgatgc cgcaacgcat       300
caaccgctag ccaaagctgc ttttacttta acgacagcaa cgccggctga taacggtcaa       360
actgtttttg tttcgcaaaa gacgaatcaa gatggtgaag tgaccattaa gcaattacca       420
acaggcaaaa taacttacga gcaaatggcc aatgctgcgg gctacgagcc actagcagcg       480
```

```
attcaaacgg cgattgtggg tgctgatggg gcacaaaaca ctgaagtaac agttgataat    540
cagcggctaa aagtgactga aaaacagcaa attatcgtgc ataaaaccaa tcaacaaggg    600
caagggttag acgatgcggc cttaaaatta actaatctgg caactgggca gacacaaacg    660
caaaagacgg tgtccgggca actacacttt actgagttga acccaggacg gtatgagatt    720
caggaaacaa aagcaccaac tggctatcag ttggatcaaa cacctcagtt tgtgacgatt    780
aaagtccatg aaaaacggtt ataccaagtc cgctttgctg ataaacgtga agtgactgcg    840
ccaatcagtc cattgcgcat ccagatttta gataatcact tgcaaggcgt tgctggtgtt    900
ttactgcgac taaccgccga tcaaccggat gaccaaggtc agaccgtttg ggaattgaca    960
actgatcgat tcggacaggc tatactcccc aatgcaagta cggggcacta tcgggttgag    1020
gttttacaag taccgaccgg gtatcaattg tcgtttgatc aaagtcaatt agatgtcagc    1080
cgctatggtg aaaatcagtt acaattacaa gctaatcgaa ttgagatgcc attgcaaacc    1140
ttaacgatta ataaaaccaa cttaaaaggg caacctttat caggtgctgt ctttaaagtc    1200
gagtcactga aactggtca gatgactaaa gttgaaacgg atcaaaccgg tcgggctgag    1260
ttgcgggacc aaaaaccagg cgcatatcgc gtaactgaag tggaagcacc acttggttac    1320
cggttagcaa ctgaacctag aattgtagcg ttgtctgaaa aatcaccgcg agcaacacaa    1380
ctaacggtaa cagatgaagc acaaatgggg cagttactga ttaagcatac aactaaaaag    1440
ggcgcaccga ttgcaaaggc ctactttgag gttaaggatc aaagtggtcg agaagtcggt    1500
tattatcaaa ctgatagtca aggacagatt aaattaaccc agctagcagt ggggcaatat    1560
actgttcaag aaatcaaggc accaactggg tatgaaatta tccggcagt gacaaaggtg    1620 gccattacgg atcgcaaaac ggcaacggtc gccattaagg ctgagcaaca agcacccgat    1680
gttaaattgg ggagtttgt attgatcgat agggatcaga aaacgcagtt agcgattgct    1740
agtgcaactt atcgattgga aacgttagct ggtcaggcgg ttcggccaga aattgtagtg    1800
ggtgcaactg gtcaagtcgt agttaacgac ctcacacctg gtcaatatcg actcgtacaa    1860
ttgacggcgg cacctagcta tcaaaaacaa actaacgatc aaatcatcga gattaaacag    1920
gatgcgcaac ttaaacaagt gacgattgaa agtcatcagt cacaagggac agtcattgta    1980
aatcaagtag atggcaatac gaaccaagct ttggttggag cgaaatatga attacaaaat    2040
caaagtggta aagtgcttgt cgaaaacttg aagagtgatg aacatggtca agttcgcatc    2100
acacatctcg atcctgatac gtaccgtttg gtgcaagtat cggcaactaa gggctatgac    2160
ccgcttaaaa agccgattgt ctttacgata accaatcgct aa                      2202

<210> SEQ ID NO 11
<211> LENGTH: 456
<212> TYPE: DNA
<213> ORGANISM: Lactobacillus sakei
<220> FEATURE:
<221> NAME/KEY: misc_feature
<222> LOCATION: (1)..(456)
<223> OTHER INFORMATION: LSA0529

<400> SEQUENCE: 11
atgattaaac cagtattatt agatgagcaa ttatgctttt cgatttatcg cgcacagaaa     60
gcttataacc acttttatgg aaaggtctta aaacctatg gcttaactta tccacaattc    120
atcgcaatgt tagcattgtg ggaacatggg acaatgtcag ttaaggaatt aggtcaccat    180
ttagaattag atagtgggac attaacacca ctattgaaac gcctagaagc ggatggttgg    240
gttgatcgta agcgtgcatc tgatgatgaa cgtcgcgttg acgtttcatt aacagagcaa    300
```

```
gcagaatcgc aaaaacttga aatttacgaa cgtgttggta actgtaccaa ctacctagct    360
ttcacaagcg acaaatatca tgacttacgt caaagcatga acgaagtcga aaacattta    420 aatgctattc aagctgatac tgatcgattt gcttaa                              456
```

<210> SEQ ID NO 12
<211> LENGTH: 849
<212> TYPE: DNA
<213> ORGANISM: Lactobacillus sakei
<220> FEATURE:
<221> NAME/KEY: misc_feature
<222> LOCATION: (1)..(849)
<223> OTHER INFORMATION: LSA0439

<400> SEQUENCE: 12

```
atgaagaagt ggggcttttt acttagcggt ggttttctag tagcaattat tgtaggaata     60
ttactgataa atcagcgtcc aaaccaagca agacaacaag caaatcgtgt ccatgacagt    120
gcaccaactt tttatttaca tgggtatggt ggctctggtc gttcgagcga tagtatgatt    180
gcggcggcag aagagcgagg tagggctact aaggtattaa ccgcaattgt cagtcggacg    240
ggacaagttg aattagaggg gcattggaca ggcaatacaa cacgaccgat tatccaggtg    300
atttataaga ataatcgcaa tgccaattac cggcaaaatg gtgaatggtt caaacgggta    360
ttgattgcgg ttaaccggca gcatcatttt aaacaattta atgtagtcgc tcattcgatg    420
ggtaatttaa cattagcttt ctatctggca ataatgctc agaataaaaa aatgccacaa    480
ttaactaagt tcgtttcgat tgcggggcac tatgctggta ttatcgggat ggatgatcgt    540
gcaaatcaaa atcatctggc taaaaatggc cgcccacagc agatcaacgc cacttaccgg    600
caactaatgg gattgagaca cagattaccc aaaaatcaaa ttcaatactt aaatatttat    660
ggggacttat cagatggtag tgattctgat gggcgtgtta gcaatgtctc ttcacaatcg    720
ttgcgatatt tagtggcacc aagagcaaaa tcatatcaag aagttcaatt taagggctcg    780
aatgcccaac atagcaaact atatgaaaac gaagctgtta ataaagcggt aatcgatttc    840
ctatggtaa                                                            849
```

<210> SEQ ID NO 13
<211> LENGTH: 1041
<212> TYPE: DNA
<213> ORGANISM: Lactobacillus sakei
<220> FEATURE:
<221> NAME/KEY: misc_feature
<222> LOCATION: (1)..(1041)
<223> OTHER INFORMATION: LSA0572

<400> SEQUENCE: 13

```
atggcaacaa ataatttagt tttgaagaca gctgacattt gtgatattcg tgatattgaa     60
gaggcgcggg caacaatcaa accttacatc cgggaaacac cattaattca atcgatgttt    120
ttaagccgga atgtcgctaa gggcaatgtt tatctgaaat tagaaaacat gcaattaaca    180
ggctcgttca aatttagagg tgccaataac aaaattaatc atttaactga agaacaacgt    240
caacgtggga ttgtaacagc atcagctggt aaccatgcac aaggtgtcgc attaaccgct    300
aagttattgg gaattgatgc aacagttgtt atgccagaag aagccccaat tgctaaacaa    360
gaagcaacgg ctggttacgg tgctaacgtt gtcttacacg gtgcaacttt taacgatgca    420
cgtttataca tggaacaatt agcagaagaa aaaggcatga caatcgttca tccttacgat    480
gatcgtgaag tcatggctgg ccaaggcaca attggtcttg aaatcttaga tgaaatttgg    540
aatgtcgaca cagtaattat ccctgttggt ggggcggct taatttcagg tgtggcaaca    600
```

```
gctttgaaat ctttcaaccc atcaattcac attatcgggg ttcaatctga aaacgtgcat    660
gggatggcgg cttcaatcga tgctggcaaa attacaagtc accatgatga cttcacatta    720
gcagatggta ccgatgttgc tattccagga gacttaactt acccagttgt tcaaaaccta    780
gtagacgaat tcatcttagt cactgaagac gaaatcgcaa tggcaatgac cgacttgatg    840
caacggacta agattgtcac agaaggtgcg ggtgcattac caacagctgc cttattaagt    900
ggcaagattg atcctaagtg gcttgaagat aagaacattg ttgcgatggt ttcaggcggt    960
aatgttgatt taacacgggt ttcaggtatt attgaacacc tcttcaaacc agcagacaca   1020
agcaagggtg ttgttggata g                                             1041

<210> SEQ ID NO 14
<211> LENGTH: 960
<212> TYPE: DNA
<213> ORGANISM: Lactobacillus sakei
<220> FEATURE:
<221> NAME/KEY: misc_feature
<222> LOCATION: (1)..(960)
<223> OTHER INFORMATION: LSA0219_b

<400> SEQUENCE: 14
ttgagtctag aatatactat tggttattct acaatcgtat tagttatagg gttatttatt     60
agatcaattc cccaaacaag cactttatta tttggaacta ttttagtagg tagtgcaatt    120
gccatgtgta acgtattaat tccaagttta ataaaaagag aatttaatca tcgcttaggc    180
ctaattactg gtatttattc aattagtatg aatttatgtg gggcaattgc atctggagtt    240
agttttccat tagctaataa tctaaatcta ggttggaata attcacttag gatttggctt    300
attttggctt taattgcttg tatcgcatgg attccacaat tgaaaagaca tgataaacca    360
gataagatag aggaattacc tatagagaat agtatttggc attcaaaaac tgcgtggcaa    420
gttactatat ttatgggcct acagtcacta gtattctacg tgttagtcgc gtggttacct    480
gaaatgctta ttcaaaaggg attcactgca gaacaagctg gttatttatt gtcaatgatg    540
caattatttt tattaccatt tacatttata attccaatta ttgctgggag ggtcaaaaga    600
cagagtaaaa ttgccataaa cacatcaatc ctaatgtgtt taggaattag tgggcttttt    660
ataaataata ctattattat tattataggga attgcttttta ttgggatcag tggtggctgt    720
gcatttggac tatcaatgat gttttttaac ctaaaaacaa gaaatgcaag agaagggggca    780 gaactatcag gcatggctca atcaattggt tacttgttag ctgcaattgg cccaactctc    840
tttggcttta tgcatgatat gactcataat tggaatgtat cattaattat tttaattgtg    900
actgctattt tattagggggg atttggattc tttgctggtg aagataatta tataaattaa    960

<210> SEQ ID NO 15
<211> LENGTH: 144
<212> TYPE: DNA
<213> ORGANISM: Lactobacillus sakei
<220> FEATURE:
<221> NAME/KEY: misc_feature
<222> LOCATION: (1)..(144)
<223> OTHER INFORMATION: LSA0564_a

<400> SEQUENCE: 15
atggagagaa taagtgaata caaagtattg aataataatg ttttagctgg agtacaaggt     60
ggtaaaaaga aaagggtgg cttcttttgg cattattttg gagatcctat tgttagtttt    120
ggtaaaggat ttattggata ttaa                                          144
```

```
<210> SEQ ID NO 16
<211> LENGTH: 165
<212> TYPE: DNA
<213> ORGANISM: Lactobacillus sakei
<220> FEATURE:
<221> NAME/KEY: misc_feature
<222> LOCATION: (1)..(165)
<223> OTHER INFORMATION: LSA0564_b

<400> SEQUENCE: 16
atgaataaaa aattggatag tttcagcagt attgaagatg ataaattagg actagttatt      60
gggggacgaa ataatctagc atatggtctt ggtaagttag ttcgtgccgg tgttgatata     120
ggaatagcga ttgggagcaa aggtcgctac aaaccaagac actaa                     165

<210> SEQ ID NO 17
<211> LENGTH: 669
<212> TYPE: DNA
<213> ORGANISM: Lactobacillus sakei
<220> FEATURE:
<221> NAME/KEY: misc_feature
<222> LOCATION: (1)..(669)
<223> OTHER INFORMATION: LSA0564_c

<400> SEQUENCE: 17
ttgaatacgt tagaagtgat tagccagaga agggctgttg gtgggtttgt attattaata      60
ataggttatt tattgagtag tcgtattagt ctagaaattt cttttttttaa tatatcttgc    120 ttattttttaa tcttattttc gtatagtgca ctgattgtat tatttggtta tcaatcaaca   180
aaagatttat taaaaccgct aaaacgaccg tttgtgagaa aaatattatc agcagttgga    240
ttaagttttc taattgtctt tggaataagt attgtgttaa tgatgttttt tggagaagtg    300
gcggtcactc agaatggcaa tattccattc ctgaagtcaa ttactgtaaa gtggcaatta    360
gtgagcttgc taattatctt tttaaacata ataggtgaag aattatgggt cgctgggatt    420
gttttaccaa tagccacttg gctaacagaa tataaattta attggctatt ggctaattta    480
attggctgtt taattttttgc attaatccat ttagagattt ataagttcaa tattgcaata   540
tgtctaattg taggattttc taggtatgga ttttcgatgg cttggaaatc gaatgataca    600
ttaagaggtg ggatatatgc gcatctatta tatgactcct tattgttagc tgtgaatata    660
ctattataa                                                             669

<210> SEQ ID NO 18
<211> LENGTH: 336
<212> TYPE: DNA
<213> ORGANISM: Lactobacillus sakei
<220> FEATURE:
<221> NAME/KEY: misc_feature
<222> LOCATION: (1)..(336)
<223> OTHER INFORMATION: FGP21-0001

<400> SEQUENCE: 18
atgaagagat tatgcatatt agcttatcaa gggctgccat ttctgattga aatttggtt       60 atctttaata agaaggaacg gaattttgtg aagaagttaa acaatagaat cgatgaacta    120
tcgatgagtt ggcaagtaga acttgatagc tcatttggaa atattagtga tattgaagtc    180
aaagcaccgc aagccgtgtt attaaaaaat ggcttgcgat atcgttttaa tactggcagc    240
ttccctaaaa atgatatcta tcaattggga gctttagaat acaagaagg tgatattgat     300 gccgttattt cttttttgaa gcatttagag aggtag                               336

<210> SEQ ID NO 19
<211> LENGTH: 186
```

```
<212> TYPE: DNA
<213> ORGANISM: Lactobacillus sakei
<220> FEATURE:
<221> NAME/KEY: misc_feature
<222> LOCATION: (1)..(186)
<223> OTHER INFORMATION: sspA

<400> SEQUENCE: 19
atggaaaagt ttattgaatt atctttaaaa gaagtaacag caattacagg tggaaaatat      60
tatggtaacg gtgtacactg tggaaaacat tcatgtaccg tagactgggg aacagctatt     120
ggaaatatcg gaaataatgc agctgcaaac tgggccacag gcggaaacgc tggctggaat     180
aaataa                                                                 186

<210> SEQ ID NO 20
<211> LENGTH: 297
<212> TYPE: DNA
<213> ORGANISM: Lactobacillus sakei
<220> FEATURE:
<221> NAME/KEY: misc_feature
<222> LOCATION: (1)..(297)
<223> OTHER INFORMATION: spiA

<400> SEQUENCE: 20
atgaaaatat tgaagtggta ttcaggtggt aaggatcgcg gagaacgggc aaatgatatt      60
ataggccaat tgttgctaga tctgaaccat gatccaaaaa atgaacattt agaagcaata     120
ttaataaatt atcagaatga aattaaaagg aaagaaagtt cggtgccatt tattttgagt     180
cggatgaata tatcaatagc caatacaatc agaagagata ggctcatttt aaccgatttt     240
caagaagata aattgaaatt gttaactgcg ttgtctaata taagatatgg ctattag        297

<210> SEQ ID NO 21
<211> LENGTH: 821
<212> TYPE: DNA
<213> ORGANISM: Lactobacillus sakei
<220> FEATURE:
<221> NAME/KEY: misc_feature
<222> LOCATION: (1)..(821)
<223> OTHER INFORMATION: FGP332-0001

<400> SEQUENCE: 21
cgcggttgac gataccctct ctccaaatga gcaattacaa ctgcgctatc aagcgctgca      60
tcatcaattt gttgcgagta gcatcgccgt taaacaatgt catgaattga tgcccgatgc     120
gaaaattggt tcaatgttgg cgcggatgca aagttatcct aaaacaccga accccaccga     180
tgtccgtcaa gcgcaagaag atgatgaatt gaatctcttt ttcacagatg ttcaggtccg     240
tggcgaatat cccaactata tgaaccgtta cttcaacgac cacgcatcg aacttgaaat      300 ggcacctgac gacttacaaa taatcaaaga ttatccggtc gattatttaa gcttcagcta     360
ttacatgtca atggtcagct cagctaaacc cgccggtgaa aaaacagctg gcaacttaat     420
cctcggtgaa aagaatccgt atctcgaatc aagcgactgg ggttggcaaa ttgatcccgt     480
cggtttacgg attaccctca caatctctgt ggaacgctat ggtgtaccac tattcatcgt     540
cgaaaatggc ttaggcgcaa tcgataaggt tgcagctgac ggtcaaattc atgaccctta     600
tcgtattgac tacatgcgca acacatcgc acagatgaaa gaggccgttc aagacggcgt     660
ggatctaatg ggctacacca tgtggggacc aatcgactta attagtgcct ctacctctga     720
aatgtccaag cgctacggct ttatttacgt cgaccaagat gatgacggca acggtacgct     780
cgaacgacgc cgtaaagact cgttctactg gttcaaaaac g                         821
```

```
<210> SEQ ID NO 22
<211> LENGTH: 1335
<212> TYPE: DNA
<213> ORGANISM: Lactobacillus sakei
<220> FEATURE:
<221> NAME/KEY: misc_feature
<222> LOCATION: (1)..(1335)
<223> OTHER INFORMATION: FGP332-0002

<400> SEQUENCE: 22
agcacgaaaa tcccagtcga agttgaacct gtcgaaattg aaagaaagt tttaaatgaa      60 actgaaaaag aaacgacgta ccaaaaagcg acggtcgggc atgtaaatga tgttcttgat    120
taccaagtga agttaacagt cagcagtaac ggagctgata tgtctaacgg tgtcttggcc    180
gatgacctag ctaaggaagg gttagaatta gtgccgggct ctgttaaatt gacatatagc    240
gataagacag ttgaaacccc agcagatgtt aaacagatta atttgaaaaa aatgacacct    300
ggacagaatg tagtattaac ctataaggct aaagtcaaag aaggtgttgt gataggcaca    360
gtgcttaaaa atattgtttt atattctggg gaacaagcta atcagggtgt tatgaacggg    420
caagctgacg cgtcagtaac gattgaaaag acgaagaata gtgacgttca ctttagttat    480
attgatcgtg aaacggggca gcagattgct aatgaagtcg ttgcaactgg gccaattaat    540
gccaaaatat cagcattaaa agcaactgat attagcgatg ggcaagatcc taataagatt    600
cggcccgcct acattgaagg ttatacgcca gttgatttta cgacggcaac tgatttaaac    660
gctgcggtct atgcggatat taaagatgtt gatccagtaa ttgaagaaaa atcggtgacc    720 tatacttta gatatgaaaa aacgcgctta gcgattacgg cgttaccaag taaactgaat    780
tttggtaaat cgacgatac gcaaagtgaa cggacgtttt atttgccggc acaaattgag    840
aaaccagctg atgaaaaaac accatatggc attgaaatct ctgattattg ggcattaag    900 ggctggacgt tgagtgttgc acaggaacaa caatttcatg gcagtgccac gatagattta    960
aaggaacaag tagttgagct gtccggcgca caactccagt ttaataacgc aacattgagc   1020
acgcatacgg aaggtaataa gtctgttttcg aatttgcagg ataaagtagt aactaaatca   1080
aactttaact tggtacccgg ggctgagccg ttagaattag ttgaatacga acgaaaaggc   1140
cagtacctta atcaagacgg cgacaataaa ggcggggtca gttatgatat ccctggctat   1200
tcagttcata aatatcaatt tggtgacgca agaacggctg attacagtat tggcctgcat   1260
gtcccagaaa cgactgaacg ttaccgtaca gaatacacat caacattgaa gtggcattta   1320
acggttgcgc cataa                                                    1335

<210> SEQ ID NO 23
<211> LENGTH: 391
<212> TYPE: DNA
<213> ORGANISM: Lactobacillus sakei
<220> FEATURE:
<221> NAME/KEY: misc_feature
<222> LOCATION: (1)..(391)
<223> OTHER INFORMATION: FGP332-0007

<400> SEQUENCE: 23
acagcttata ctgatggcac aagtagtcta aatgatggtt tacaagaact tgctaaaaac     60
aacaaagatt taaataacgg tgcaacaagt ctagcatctg tgttaaagaa cttaaaagca   120
ggtagtcaaa agatttctgc tgggttacaa aagatgcaat cacaacttaa cagcaaccca   180
acattcaaag atgatgcaag ttataatgca gccgttgcgc aatatacagc attaaatggt   240
atgattgctc aagttgaaag tacgattcct gcattacaaa cagatttaaa tgcgattcct   300
gatcaagttg ttgcaacaac tgatttcaat gcaaaagcac aagcaattat tgatgctgaa   360
```

```
aaacaagcag gtattgtctt cagtgcacaa c                                       391
```

<210> SEQ ID NO 24
<211> LENGTH: 466
<212> TYPE: DNA
<213> ORGANISM: Lactobacillus sakei
<220> FEATURE:
<221> NAME/KEY: misc_feature
<222> LOCATION: (1)..(466)
<223> OTHER INFORMATION: FGP332-0008

<400> SEQUENCE: 24

```
gatgacgcca ctaactgttt agtgcaccaa tgctatttaa gagttgattt aattttagtc     60
gttgctgttt ttgaatcgtt cgacattgat ttaattgttg ttccacttcc gactcttcag    120
tcaatcgcat cgcattgaca aaatcctttg cagcagtcac ataatgctta ataaccatct    180
gtaattgctc atgtaatgcg acaaattccg ttggcggttg aatacgcgca atttgatcaa    240
caaattgatc gaggacagtt aaattctgtc tggaatagtg attaagtaat tgtaaatttt    300
catctaccaa tcctttaccc cgcataacat ttttactagt ttgcgcatat tcactaaaaa    360
ccgtttcgaa gacaataaac cgctctaaaa accgattcca ttggatcaca taagcttgtg    420
ccgatagctg aattgttggt tgtaacattc taatcgcctc cttgac                    466
```

<210> SEQ ID NO 25
<211> LENGTH: 132
<212> TYPE: DNA
<213> ORGANISM: Lactobacillus sakei
<220> FEATURE:
<221> NAME/KEY: misc_feature
<222> LOCATION: (1)..(132)
<223> OTHER INFORMATION: FGP332-0009

<400> SEQUENCE: 25

```
ccacgttggt caaccggaac cacaaggaaa taatgcgagc ttaccaggtg gtggtattat     60
acttaaacag tattacggtg cacaaggaat aaagattttt aaactaacgc taaaccagg    120
aaacaaggtc aa                                                         132
```

<210> SEQ ID NO 26
<211> LENGTH: 768
<212> TYPE: DNA
<213> ORGANISM: Lactobacillus sakei
<220> FEATURE:
<221> NAME/KEY: misc_feature
<222> LOCATION: (1)..(768)
<223> OTHER INFORMATION: FGP332-0010

<400> SEQUENCE: 26

```
tcaggaatta gatgaatatg tgattactag cgaaatacgt aagaatatgg gaactttttt     60
tgaggcgtac gtaaagtcgt tagagcaacc aactgatcaa atgggtgtct ggatatctgg    120
attctttggt tctggtaaat ctcatttctt aaagatatta agctacctaa ttgatagtca    180
aaagacagtt aaaggacgac gacctatatc gtttatcgaa ggtaagtttg aagaaaatga    240
tgaaacatta gcgctaataa aacgcgctag tgaacaacct aatcaggttg cattatttaa    300
tattgaatct aaggctgagg ctgacagtgt gaatagtaaa tcggctgttg ttaaagtctt    360
taataaagtt ttgaatgaat tacgaggctt ctcaggtgct aatgcatgga ttgcggagat    420
ggaagagaca cttgccaata acggacagta tgaacagttt aaaactgctt ttgagcgtat    480
tgctgactta gattgggtgg aaggccggga ggaattttt tataatgagg actcggtaat    540
tgaggcctta agtgaagtaa cagaaatgac gattgagagc gcacgacact tcatagaatc    600
```

```
tggggaagct aattatgaaa ttagtgatga gtcatttgct aaaaaagtga agcgatacgt    660
tgatcaacag ccagataatt atcatttagc ttttttagca gatgagatgg ggcaatatat    720
tgctgataat ggtcaattaa tgttggattt acagatggtt gttgaaga                768
```

<210> SEQ ID NO 27
<211> LENGTH: 522
<212> TYPE: DNA
<213> ORGANISM: Lactobacillus sakei
<220> FEATURE:
<221> NAME/KEY: misc_feature
<222> LOCATION: (1)..(522)
<223> OTHER INFORMATION: FGP332-0011

<400> SEQUENCE: 27

```
gctaaatctt gaaagctaac ggttgattgg ctagcaaacg tcgtgaattg atcgagatta     60
atttgaagct gttcttgacc gaggtattga gattcgatgg tcgtatcaag gatttcttga    120
tctgaaaaga ttagggcaac ttggtctgtc tttagtgcat tactaatttg atccaccgca    180
atgaattctt tggtgatttg cacatcatca cggttaggca cgagggttag cggtccggga    240
atcgttgcgc caattatcgt aaagtgctga ccgcgatcga aatttttgaat tttagtcagc    300 atcgtttgac tagtcgtcaa aagttgttca gcttctcgag cggcaagctc gcctgttggt    360
gtcagtttaa tgcgattagc ttgacggtca acagctggaa caccaaaatc ctcttccaac    420
ttttgcatgc cgcgtgtgac ggatggctgg gtgatgttca aagcagcagc agttttcgtg    480
agggtgccag tcttggcgaa ggtcgtcaat tgttctaata aa                       522
```

<210> SEQ ID NO 28
<211> LENGTH: 597
<212> TYPE: DNA
<213> ORGANISM: Lactobacillus sakei
<220> FEATURE:
<221> NAME/KEY: misc_feature
<222> LOCATION: (1)..(597)
<223> OTHER INFORMATION: FGP332-0012

<400> SEQUENCE: 28

```
acattggagg aaattcttga tgaaagcaat cgttgtctca aaggctggtg ggccagaagt     60
ccttacatat accgacgttc caaaaccaac aattaagtca ggctggtcac tcgttaaagt    120
gatgggtttt ggcattaacc gctccgaaat tttcacgcgg gaaggcaagt ctccctcggt    180
tcaattcccc agaatcctcg gcattgaggc tgttgggatg attgctgaat cttccgatcc    240
ggaacaactg ccagttggtc aaaaagtgat ttcaattatg ggcgagatgg gccgcgcctt    300
tgacggtagc tatgctgaat acgtcttact acccaatgaa caaatctatc cggttgaatc    360
gactttaagc tgggctaatc tcgccgcgat tcccgaaacc ttctatacag ccttcggaat    420
tttcaaaagt ttacaaatta ctaaaagcga ccatgtttta gtcagagcag ccactagcgg    480
tgtcggtatt gcagtgatga aattaatcaa aggatatgct gccagtatct ccgtaactgg    540
gaccacgcgc tctgcaaata aatctgatca attattagca gccggctttg atgatgt      597
```

<210> SEQ ID NO 29
<211> LENGTH: 486
<212> TYPE: DNA
<213> ORGANISM: Lactobacillus sakei
<220> FEATURE:
<221> NAME/KEY: misc_feature
<222> LOCATION: (1)..(486)
<223> OTHER INFORMATION: FGP332-0013

<400> SEQUENCE: 29

```
acttgagatc gatcgggttg cggtccatcc cgatcgcaaa ggtccgtaac ttcttgcccg      60
gcattaactt agatgcgatc gagcaaacca gggaagaatc caggcccccg gacaacaggt     120
agcccaccgg agcgtcagcg tggagccgct tttccacccc cttgaccagg taatcacgga     180
tgccggtcgt ggcttcttca aagctcggcg tgtgcatccg ggtaaccatg gccgggtcgc     240
ggtaggtaac gaacttttcg ccgtcgtagt agtggcccgg tgggaacggg aagatttggt     300
cgcacaagtc catcagggtc ttggccgtgg aaccaaaggc gatttcgccc ttctccttgg     360
tgtagccgta aaacattggc cggatcccga tcgggtcacg tccggccacg accttcttgg     420
ccaccttgtc gtataagacg aaggcgaact cggcgtcgag catcctgcac atggtgtcca     480
gcccgt                                                                486
```